US008198218B2

(12) United States Patent
Gilon

(10) Patent No.: US 8,198,218 B2
(45) Date of Patent: Jun. 12, 2012

(54) HETEROCYCLIC COMPOUNDS, COMBINATORIAL LIBRARIES THEREOF AND METHODS OF SELECTING DRUG LEADS

(75) Inventor: Chaim Gilon, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 12/474,318

(22) Filed: May 29, 2009

(65) Prior Publication Data

US 2010/0022499 A1    Jan. 28, 2010

Related U.S. Application Data

(63) Continuation of application No. 11/086,722, filed on Mar. 22, 2005, now abandoned, which is a continuation of application No. 10/882,636, filed on Jul. 2, 2004, now abandoned, which is a continuation of application No. PCT/IL03/00008, filed on Jan. 2, 2003, which is a continuation of application No. 10/034,212, filed on Jan. 3, 2002, now abandoned.

(51) Int. Cl.
*C40B 40/02* (2006.01)
(52) U.S. Cl. ............. 506/15; 514/183; 506/8; 506/10
(58) Field of Classification Search .................. None
See application file for complete search history.

(56) References Cited

U.S. PATENT DOCUMENTS

| | | | |
|---|---|---|---|
| 5,723,575 A | 3/1998 | Gilon et al. | 530/317 |
| 5,811,392 A | 9/1998 | Gilon et al. | 514/11 |
| 5,874,529 A | 2/1999 | Gilon et al. | 530/317 |
| 5,883,293 A | 3/1999 | Gilon et al. | 562/455 |
| 6,117,974 A | 9/2000 | Gilon et al. | 530/317 |
| 6,265,375 B1 | 7/2001 | Gilon et al. | 514/9 |
| 7,169,899 B1 | 1/2007 | Deslongchamps et al. | 530/371 |

FOREIGN PATENT DOCUMENTS

| | | |
|---|---|---|
| EP | 0 564 739 A2 | 10/1993 |
| WO | WO 93/09133 | 5/1993 |
| WO | WO 99/31121 | 6/1999 |
| WO | WO 99/65922 | 12/1999 |

OTHER PUBLICATIONS

J.F. Reichwein, "Synthesis of Cyclic Dipeptides by Ring-Closing Metathesis," Eur. J. Org. Chem. 2000(12): 2335-2334.
Schmitz E.: 'Cyclische peroxyde aus hydrazinverbindungen' Justus Liebigs Annalender Chemie vol. 635, 1960, pp. 73-82.
Katritzky et al.: 'The conformational analysis of saturated heterocycles. Part 92. Conformational equilibriums of 1,2-dioxa-4,5-diazacyclohexanes' J. Chem. Soc. Perkin Trans. 2: Physical Organic Chemistry (1972-1999) vol. 8, 1979, pp. 1133-1136.
Chaim Gilon et al., XP002912704, "Backbone Cyclization: A New Method for Conferring Conformational Constraint on Peptides", Biopolymers, vol. 31, No. 3, pp. 745-750 (1991).
PCT Search Report for WO 03/059876 A3 published Jul. 2003 by Gilon (6 pages total).
Miller et al., "Catalytic Ring-Closing Metathesis of Dienes: Application to the Synthesis of Eight-Membered Rings" J. Am. Chem. Soc. 1995, 117, 2108-2109.
Luning, "Synthesizing Macrocycles under Thermodynamic Control-Dynmaic Combinatorial Libraries and Templates" J. Incl. Phen. & Macro. Chem. 2004, 49, 81-84.
Qvit et al., "Synthesis of a Novel Macrocyclic Library: Dsicovery of an IGF-1 R Inhibitor", J. Comb. Chem., 2008, 10,256-266.
Parsons, J. A. Peptide Hormones. Baltimore: University Park Press. 1976, pp. 1-6.
Roy et al., "New thionitrites: Synthesis, Stability, and Nitric Oxide Generation" J. Org. Chem. 1994, 59, 7019-7026.

*Primary Examiner* — Christopher M Gross
(74) *Attorney, Agent, or Firm* — Winston & Strawn LLP

(57) ABSTRACT

Heterocyclic compounds having a relatively flexible backbone are used to create combinatorial libraries that permit screening for lead compounds and selection of drug candidates for a variety of uses in human and veterinary medicine as well as in agriculture. The compounds of the library generally differ in ring size and chirality of substituents on the ring. Also disclosed are methods for providing and screening these libraries, preferably in an automated or computerizable manner, such as by using a computer program to virtually screen the compounds in order to identify those that are predicted to have bioactive conformations that should give rise to desirable biological effects.

21 Claims, 4 Drawing Sheets

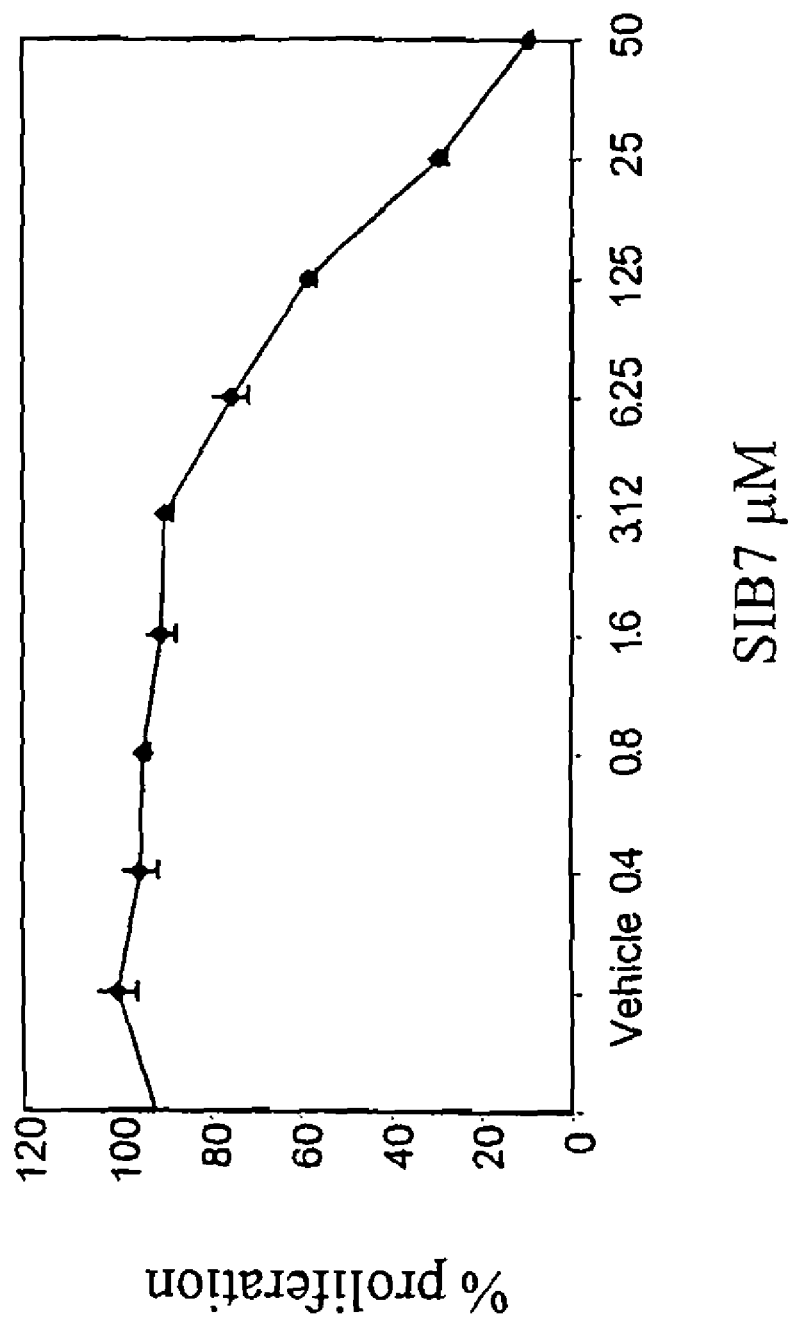

HETEROCYCLIC COMPOUNDS, COMBINATORIAL LIBRARIES THEREOF AND METHODS OF SELECTING DRUG LEADS

CROSS-REFERENCE TO RELATED APPLICATIONS

This application is a continuation of U.S. application Ser. No. 11/086,722 (now abandoned) filed Mar. 22, 2005, which is a continuation of application Ser. No. 10/882,636 (now abandoned) filed Jul. 2, 2004, which is a continuation of International Application PCT/IL03/00008 filed Jan. 2, 2003, which in turn is a continuation of U.S. application Ser. No. 10/034,212 (now abandoned) filed Jan. 3, 2002, the entire content of each of which is expressly incorporated herein by reference thereto.

FIELD OF THE INVENTION

This invention is generally in the field of combinatorial chemistry and use of combinatorial libraries of heterocyclic compounds to select and develop new drugs. More specifically, the present invention provides novel heterocyclic compounds that have are relatively flexible backbone, combinatorial libraries comprising these compounds, which may be used to screen for and to select drug candidates for a variety of uses in human medicine, veterinary medicine and in agriculture.

BACKGROUND OF THE INVENTION

An important objective of combinatorial chemistry is to generate a large number of novel compounds that can be screened to identify lead compounds for pharmaceutical research and drug development. Theoretically, the total number of compounds which may be produced for a given library is limited only by the number of reagents available to form substituents on the variable positions on the library's molecular scaffold. The combinatorial process lends itself to automation, both in the generation of compounds and in their biological screening, thereby enhancing greatly the opportunity and efficiency of drug discovery.

Combinatorial chemistry may be performed in a manner where libraries of compounds are generated as mixtures, while the complete identification of the individual compounds is postponed until after positive screening results are obtained. However, a preferred form of combinatorial chemistry is "parallel array synthesis", (also called Multiple Parallel Synthesis, MPS) where individual reaction products are simultaneously synthesized, but are retained in separate compartments [Geysen et al. (1984); Houghten (1985)]. For example, the individual library compounds can be prepared, stored, and assayed in separate wells of a microtiter plate, each well containing one member of the parallel array. The use of standardized microtiter plates or equivalent apparatus is advantageous because such an apparatus is readily accessed by programmed robotic machinery, both during library synthesis and during library sampling or assaying.

Combinatorial chemistry can be carried out in solution phase where both reactants are dissolved in solution or in solid phase where one of the reactants is covalently bound to a solid support. Solid phase synthesis offers the advantage that reactions can be carried out using excess reagents, while the solid support-bound products are easily washed free of excess reagent. The use of excess reagents may ensure high yield of each step in a multiple step synthesis. Solution phase synthesis typically requires use of one or more reaction mixture work-up procedures to separate to reaction product from unreacted excess reagent.

The first combinatorial libraries were composed of peptides, in which all or selected amino acid positions were randomized [Geysen et al. (1984); Furka et al. (1991)]. Peptides and proteins can exhibit high and specific binding activity, and can act as catalysts. In consequence, they are of great importance in biological systems. Unfortunately, peptides per se have limited utility for use as therapeutic entities. They are costly to synthesize, unstable in the presence of proteases, non selective and in general do not pass cellular membranes.

Nucleic acids have also been used in combinatorial libraries. Their great advantage is the ease with which a nucleic acid with appropriate binding activity can be amplified. As a result, combinatorial libraries composed of nucleic acids can be of low redundancy and hence, of high diversity. However, the resulting oligonucleotides are not suitable as drugs for several reasons. First, the oligonucleotides have high molecular weights and cannot be synthesized conveniently in large quantities. Second, because oligonucleotides are polyanions, they do not cross cell membranes. Finally, deoxy- and ribo-nucleotides are hydrolytically digested by nucleases that occur in all living systems and are therefore usually decomposed before reaching the target.

There has therefore been much interest in combinatorial libraries based on small molecules (i.e. molecules having molecular weight of up to about 1000 daltons), which are more suited to pharmaceutical use, especially those which, like benzodiazepines, belong to a chemical class which has already yielded useful pharmacological agents [Bunin and Ellman (1992); Beeley (2000)]. The techniques of combinatorial chemistry have been recognized as the most efficient means for finding small molecules that act on these targets. At present, small molecule combinatorial chemistry involves the synthesis of either pooled or discrete molecules that present varying arrays of functionality on a common scaffold. These compounds are grouped in libraries that are then screened against the target of interest either for binding or for inhibition of biological activity [Adang and Hermkens (2001)].

The elements of diversity in libraries of currently available scaffold based compounds having the general structure (A) shown below, are based mainly on sequential or positional diversity namely the order in which the various R groups are arranged around the ring and chemical diversity that can arise from alterations in the chemical nature of the R groups.

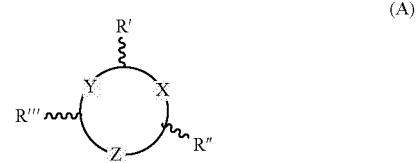

(A)

In the above structure (A), X, Y and Z represent ring heteroatoms or carbons, and R', R" and R'" represent substituents associated to the ring through a linker (showed schematically as a wavy line).

It is known from the art [Kumar S. et al. (2000)] that molecules may bind to each other if their conformations are complementary in geometry and chemistry and if their binding produces stable associations. However, most of the known libraries of organic molecules suffer from a major drawback when applied for the discovery of new drug leads based on the inhibition of peptide:protein or protein:protein or protein:nucleic acid interactions: they are too constrained and therefore lack the ability to undergo conformational complementarity, i.e. lack an ability for binding to a protein and/or a nucleic acid. This led to the preparations of extremely large libraries (consist of up to millions of compounds) and their biological screening, which in many cases results in the discovery of low affinity leads or to the lack of their discovery.

There is thus an urgent need in the art to develop new combinatorial libraries comprising molecules having a flexible scaffold backbone that are conformationally flexible and thus have the ability to undergo conformational complementarity. Such libraries will be useful in the screening for drug candidates for a variety of uses in medicine.

SUMMARY OF THE INVENTION

The present invention provides, according to a first aspect, novel heterocyclic compounds that have a relatively flexible backbone. According to another aspect of the present invention, these compounds may be used to produce new combinatorial libraries that will serve inter alia in high throughput screening assays, to screen for and select drug candidates for a variety of uses in human medicine, veterinary medicine and in agriculture.

The present invention further provides combinatorial libraries of heterocyclic compounds having a ring size of between 8 to 20 atoms wherein the members of libraries provided by the invention differ from each other (in addition to the conventional chemical and positional diversity attained by the different substituents on the ring) in at least one of two novel aspects: (a) the ring size; and/or (b) the chirality of the substituents on the ring. This leads to conformational diversity and flexibility that allows the selection of the most active compound, not only on the basis of the nature and arrangement of the substituents (attained by the known chemical and positional diversity), but also based on the ability to undergo conformational complementarity (attained by the conformational diversity and/or the chiral diversity). The present invention further provides combinatorial libraries comprising a plurality of the heterocyclic compounds of the present invention, and methods, including computerized methods, of screening the combinatorial libraries for compounds having a desired beneficial biological effect.

The present invention further provides, in accordance with another aspect, a combinatorial library comprising a plurality of heterocyclic compounds, wherein the ring size of the heterocyclic compounds is between 8 and 20 atoms, and members of the library contain at least one common pharmacophore but differ from each other by at least one of: (i) the size of the ring; and (ii) the chirality of the substituents on the ring.

In addition to the parameters above, preferably the members of the library may differ from each other by at least one additional parameter selected from:
(iii) the chemical nature of the ring;
(iv) the order of the substituents on the ring,
(v) the type of linker connecting the substituent to the ring.

Preferably, each member of the library bears at least two, more preferably at least three, yet more preferably at least four substituents. Typically the at least two substituents are independently selected from: hydrogen, a linear or branched chain alkyl, cycloalkyl, aryl, aralkyl, heterocyclyl, heteroaryl, acyl, carboxyalkyl, carboxyaryl, benzyl, hydroxybenzyl, benzyloxycarbonyl, a side chain of a natural or an unnatural amino acid or a peptide.

Within the scope of this specification and the claims which follow the term "pharmacophore" denotes any three dimensional array of descriptors which may be used to represent the therapeutic or other biological activity of a given molecule. Descriptors are expressed in terms of interactions observed in molecular recognition including but not limited to hydrogen bonding, ionic interactions, electrostatic field, van der Waals interactions, and hydrophobic interactions. The pharmacophore, may thus be defined as a model of the three dimensional orientation of a set of features which describe the physical, chemical and electronic environment of a set of molecules exerting the specific biological activity, said features comprising for example the hydrogen bond donor feature; the hydrogen bond acceptor feature, the hydrophobic region feature, the ionizable region feature, the aromatic ring feature. The three dimensional structure of the target molecule, which is complementary to the pharmacophore, can be represented by a coordinate system defining the positions of the amino acids or other molecular features interacting with said pharmacophore. The pharmacophore or its complementary target may be represented by a coordinate system that is configured in a computer readable format.

Thus, in one embodiment, the present invention provides a heterocyclic compound represented by the structure of formula I:

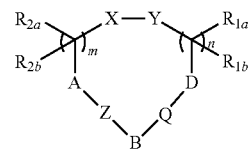

wherein

A, B and D are independently of each other $CH_2$, $C=O$ or a bond;

X and Y are independently of each other O, S, $C=O$, $S=O$, $SO_2$, $CR_{3a}R_{3b}$, $NR_4$ or $C=S$, or X and Y together form a group represented by the formula:

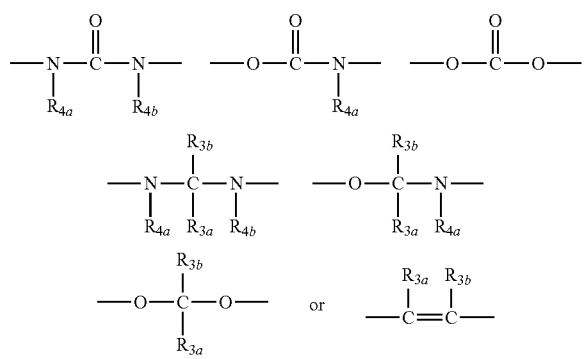

$R_{1a}$, $R_{1b}$, $R_{2a}$, $R_{2b}$, $R_{3a}$, $R_{3b}$, $R_{4a}$ and $R_{4b}$ are independently of each other hydrogen or a linear or branched chain alkyl;

m and n are independently of each other an integer of 1-6;

Z and Q are independently of each other

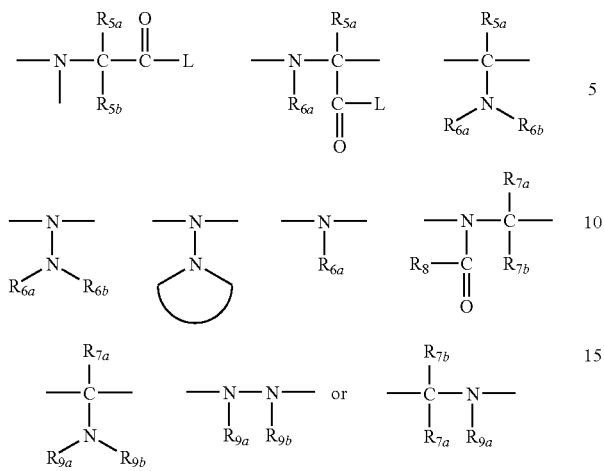

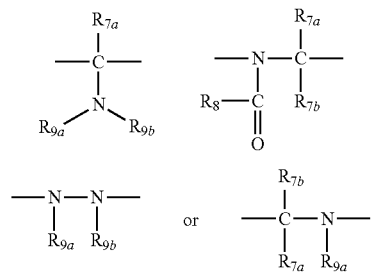

$R_{5a}$, $R_{5b}$, $R_{6a}$, $R_{6b}$, $R_{7a}$, $R_{7b}$, $R_8$, $R_{9a}$, and $R_{9b}$ are independently of each other hydrogen, a linear or branched chain alkyl, cycloalkyl, aryl, aralkyl, heterocyclyl, heteroaryl, acyl, carboxyalkyl, carboxyaryl, benzyl, hydroxybenzyl, benzyloxycarbonyl, a side chain of a natural or unnatural amino acid or a peptide;

L is hydrogen, $OR_{10}$, or $NHR_{11}$ wherein $R_{10}$ and $R_{11}$ are independently of each other hydrogen, a linear or branched chain alkyl, a side chain of a natural or unnatural amino acid, a peptide or a solid support; and

is a heterocyclic moiety containing one or more nitrogens;

or a pharmaceutically acceptable salt, hydrate or solvate thereof.

In one embodiment, the present invention provides a compound of formula I wherein A and D are a bond and B is C=O. In another embodiment, the present invention provides a compound of formula I wherein A is a bond, B is $CH_2$ are C is C=O.

In another embodiment, the present invention provides a compound of formula I wherein Q is

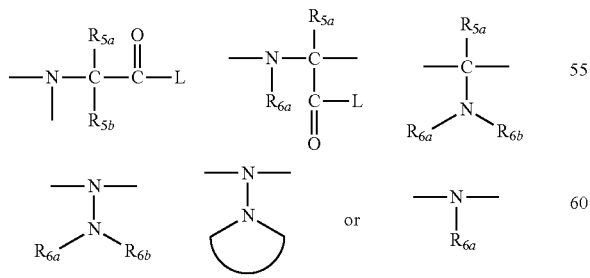

In another embodiment, the present invention provides a compound of formula I wherein Z is In another embodiment, the present invention provides a compound of formula I wherein one of $R_{5a}$ and $R_{5b}$ is hydrogen and the other is benzyl. In another embodiment, the present invention provides a compound of formula I wherein one of $R_{5a}$ and $R_{5b}$ is hydrogen and the other is hydroxybenzyl. In another embodiment, the present invention provides a compound of formula I wherein one of $R_{6a}$ and $R_{6b}$ is hydrogen and the other is benzyl. In another embodiment, the present invention provides a compound of formula I wherein one of $R_{6a}$ and $R_{6b}$ is hydrogen and the other is hydroxybenzyl. In another embodiment, the present invention provides a compound of formula I wherein one of $R_{7a}$ and $R_{7b}$ is hydrogen and the other is benzyl. In another embodiment, the present invention provides a compound of formula I wherein one of $R_{7a}$ and $R_{7b}$ is hydrogen and the other is hydroxybenzyl. In another embodiment, the present invention provides a compound of formula I wherein $R_8$ is benzyloxycarbonyl. In another embodiment, the present invention provides a compound of formula I wherein one of $R_{9a}$ and $R_{9b}$ is hydrogen and the other is benzyloxycarbonyl. In another embodiment, the present invention provides a compound of formula I wherein L is $NH_2$.

In another embodiment, the present invention provides a heterocyclic compound to represented by the structure of any of formulas II-X.

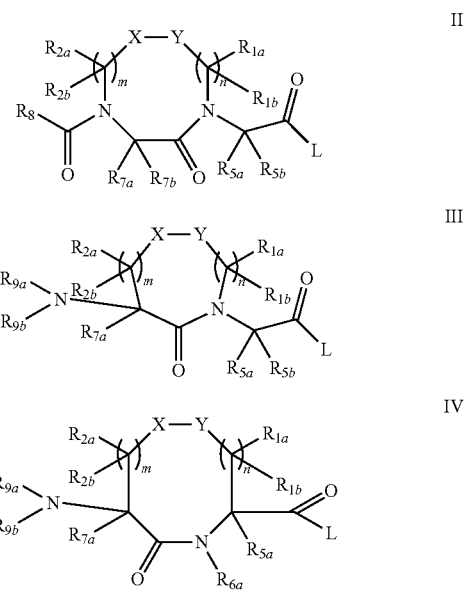

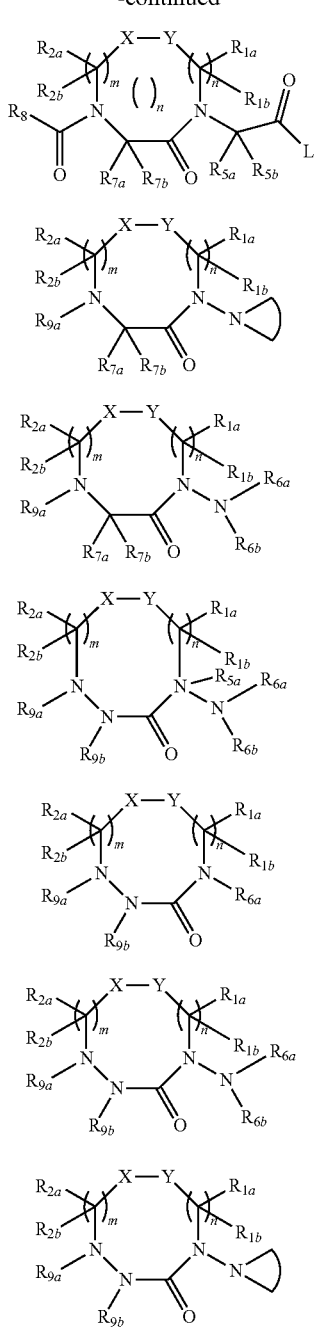

In one embodiment, the present invention provides a compound of formula II. In another embodiment, the present invention provides a compound of formula III. In another embodiment, the present invention provides a compound of formula IV. In another embodiment, the present invention provides a compound of formula V. In another embodiment, the present invention provides a compound of formula VI. In another embodiment, the present invention provides a compound of formula VI. In another embodiment, the present invention provides a compound of formula VIII. In another embodiment, the present invention provides a compound of formula IX. In another embodiment, the present invention provides a compound of formula X.

In one embodiment, the compound of any of formulas I-X comprises at least one pharmacophore potentially associated with a biological activity. In a preferred embodiment, the biological activity is mediated by a cellular component. In another preferred embodiment, the cellular component is a nucleic acid. In a particularly preferred embodiment, the cellular component is a protein. In yet another embodiment, the biological activity is proliferation, differentiation, phenotype alteration, uptake of substances by cells, secretion of substances from cells, metabolism, gene expression, protein expression, or any combination thereof.

This invention also provides, according to another of its embodiments, a combinatorial library comprising a plurality of compounds represented by the structure of any of formulas I-X. In one embodiment, the library comprises a plurality of compounds represented by the structure of formula I. In another embodiment, the library comprises a plurality of compounds represented by the structure of formula II. In another embodiment, the library comprises a plurality of compounds represented by the structure of formula III. In another embodiment, the library comprises a plurality of compounds represented by the structure of formula IV. In another embodiment, the library comprises a plurality of compounds represented by the structure of formula V. In another embodiment, the library comprises a plurality of compounds represented by the structure of formula VI. In another embodiment, the library comprises a plurality of compounds represented by the structure of formula VII. In another embodiment, the library comprises a plurality of compounds represented by the structure of formula VIII. In another embodiment, the library comprises a plurality of compounds represented by the structure of formula IX. In another embodiment, the library comprises a plurality of compounds represented by the structure of formula X. In another embodiment the library comprises a plurality of compounds represented by a plurality of structures selected from formulas I through X.

In a preferred embodiment of the present invention, some members of the library differ from the others by the size of the ring. In another preferred embodiment some members of the library differ from the other by the chirality of the substituents on the ring. In another embodiment, some members of the library differ from the others by at least one of the size of the ring or the chirality of the substituents of the ring; and further differs by at least one of the chemical nature of the ring, the substituents on the ring, the linkers connecting the substituents and the ring, the arrangement of the substituents on the ring, or any combination thereof.

The combinatorial libraries of the invention serve as a readily accessible source of diverse macrocyclic compounds for use in identifying new biologically active macrocyclic compounds through pharmaceutical and veterinary candidate screening assays, for the development of lead candidates for pharmaceutical purposes, for developing highly effective and environmentally friendly insect control and crop control agents, for use in studies defining structure/activity relationships, and/or for use in clinical investigation.

Furthermore, in another embodiment, the present invention provides methods for designing new compound libraries that have a novel type of structural complexity and diversity, and that can be screened to identify potent compounds for pharmaceutical, veterinary or agricultural use. Thus, in one embodiment, the present invention provides a method of identifying a compound having a beneficial biological activity, by (a) designing a combinatorial library comprising a plurality of heterocyclic compounds having a ring size of between 8 to 20 atoms wherein some members of the library differ from others in at least one aspect selected from the ring size and the chirality of the substituents on the ring, wherein each member of the library comprises at least one pharmacophore potentially associated with the biological activity; (b) synthesizing a plurality of compounds from the combinatorial library; and (c) screening the synthesized compounds for candidates having the desired biological activity.

In one embodiment, the biological activity is achieved by modulation of a cellular component. In one embodiment, the pharmacophore is complementary to a domain in the cellular component, which is associated with the biological activity so that the pharmacophore can bind to the domain on the cellular component and thus change the biological activity associated with the cellular component In accordance with a preferred embodiment the pharmacophore mimics a domain on a cellular component and thus interacts with another cellular component in lieu of the interaction with the domain it mimics. This may serve either as a "decoy" to eliminate the biological activity associated with the cellular component or alternatively may serve as a functional mimic of the cellular component and thus provide or enhance the biological activity normally associated with the cellular component.

In one embodiment, the method further comprises the following steps as part of the designing step (a): (a1) identifying a domain in a cellular component which is associated with the biological activity; and (a2) virtually screening the combinatorial library for lead compounds having a pharmacophore, which is capable of mimicking or is complementary to the domain. In one embodiment, the virtual screening step comprises virtual screening of the library with a computer readable data storage material encoded with computer readable data comprising three-dimensional structural determinants defining the desired domain. In yet another aspect the computer readable data storage material is further encoded with a computer program logic for controlling a processor, wherein the computer program logic comprising a procedure that enables the processor to identify a member of the combinatorial library having a specified pharmacophore.

Furthermore, in yet another embodiment, the present invention provides a computer program product for virtual screening of the combinatorial library of heterocyclic compounds provided herein for a compound having a beneficial biological activity, the computer program product comprising: (a) a computer readable data storage material encoded with computer readable data comprising three-dimensional structural determinants defining a domain in a cellular component which is associated with the desired biological activity; and (b) a computer program logic for controlling a processor, comprising a procedure that enables the processor to identify a compound having a pharmacophore to the desired domain.

Furthermore, in yet another embodiment, the present invention provides a system for identifying a compound having a beneficial biological, comprising: (a) an automated device for virtual screening of the combinatorial library of heterocyclic compounds provided herein for a compound having said beneficial biological activity, and (b) an experimental device for screening these compounds for candidates having the desired biological activity.

In one embodiment, the automated device comprises the computer program product described hereinabove. In another embodiment, the experimental device comprises (a) an apparatus for synthesizing the compounds identified in step (a); and (b) an apparatus for experimentally screening the compounds for candidates having the desired biological activity.

Furthermore, in another embodiment, the present invention provides a pharmaceutical composition comprising at least one heterocyclic compound as defined hereinabove, and a pharmaceutically acceptable carrier. Furthermore, in yet another embodiment, the present invention provides a method for the treatment of a disease, condition or disorder in a subject in need thereof, comprising the step of administering to the subject a therapeutically effective amount of a heterocyclic compound provided by the present invention.

In one embodiment, the compounds defined by the present invention are useful in the treatment of a disease, disorder or condition. In another embodiment, therapy of the disease, disorder or condition is achieved by modulation of a cellular component, for example a protein, a peptide, a nucleic acid-cellular component or a combination thereof. The compounds provided herein, either alone or in the pharmaceutical compositions are suitable for use in any subject, for example a mammalian subject or a human subject. The pharmaceutical compositions of the present invention are also suitable for use in veterinary medicine and furthermore may be used in agriculture.

The libraries of the new compounds of the present invention comprise a novel element of diversity, namely spatial diversity, that results from the varying size of the scaffold ring, the chirality of the linker or from a combination of the two. This diversity is new in the field of small molecule combinatorial chemistry. Thus the compounds of the present invention have a flexible backbone that enables conformational flexibility and accordingly these compounds have the ability to undergo conformational complementarity. The conformational complementarily enables the compound of the invention to bind to cellular targets, modulate the biological activity associated by the target and thus cause a physiological effect. Thus, the compounds of the present invention are potentially useful as drug candidates for a variety of uses in medicine.

BRIEF DESCRIPTION OF THE DRAWINGS

The present invention will be understood and appreciated more fully from the following detailed description taken in conjunction with the appended drawings in which:

FIG. 4: shows dose dependent inhibition of MCF-7 breast cancer cell proliferation in the presence of SIB 7.

DETAILED DESCRIPTION OF THE INVENTION

Figure 1:
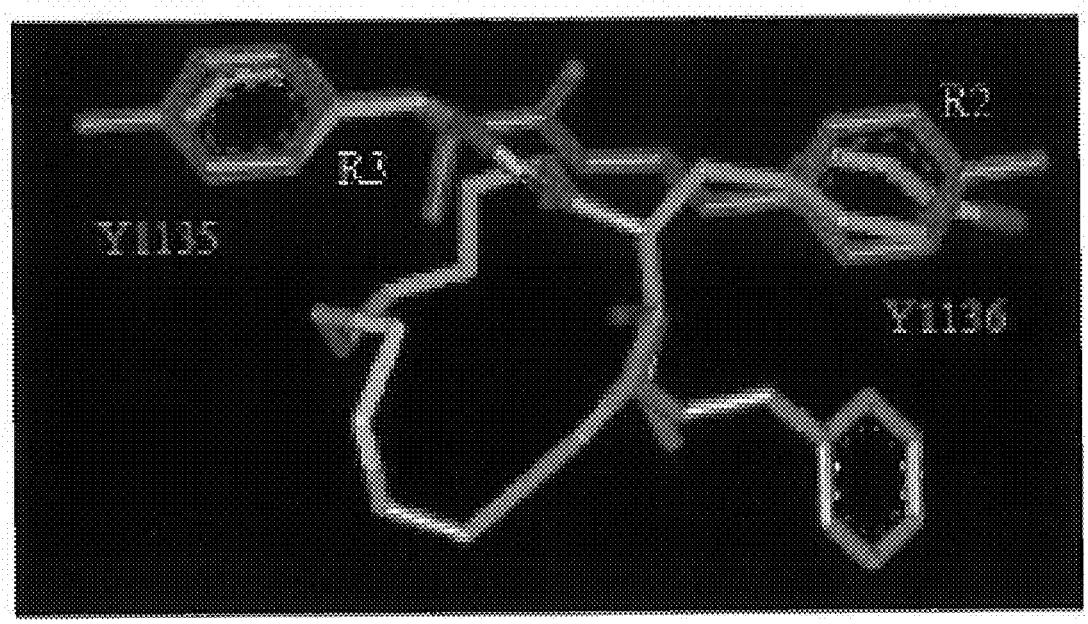
FIG. 1: shows structural super positioning of "SIB7", a heterocyclic compound in accordance with the invention, and the activation loop of IGF-IR.

The present invention provides new heterocyclic compounds that have a relatively flexible backbone. These compounds may be used to produce new combinatorial libraries that are useful, in methods including but not limited to high throughput screening assays, to screen for and select drug candidates for a variety of uses in human medicine, veterinary medicine and in agriculture.

The present invention further provides novel, ring based combinatorial libraries, comprising heterocylic compounds having a ring size of between 8-20 atoms wherein the members of libraries provided by the invention differ from each other (in addition to the conventional chemical and positional diversity attained by the different substituents on the ring) in two novel aspects: (a) the ring size; and (b) the chirality of the substitutents on the ring. This leads to conformational diversity and flexibility that allows the selection of the most active compound, not only on the basis of the nature and arrangement of the substituents (attained by the known chemical and positional diversity), but also based on the ability to undergo conformational complementarity (attained by the conformational diversity and chiral diversity). The present invention further provides combinatorial libraries comprising a plurality of the heterocyclic compounds of the present invention, and methods for screening the combinatorial libraries for compounds having a beneficial biological effect. The screening methods provided herein may be automated and/or computerized, for example by using a computer program to virtually screen the combinatorial libraries in order to identify compounds that are predicted to adopt bioactive conformations that will give rise to the desired biological effect.

Many biological processes are critically dependent on protein:protein and/or protein:nucleic acid interactions, and many drugs are small molecules known to disrupt such interactions (antagonists) or alternatively mimic one component of the interaction in such a manner so that the activity controlled by the interaction can take place in the presence of the drug and the other cellular component (agonists). The drugs, which work by interruption of such interactions (for example by the interruption of a receptor-ligand interaction) mimic a domain of one of the participants in the interaction (for example a protein).

In one case this mimic creates an antagonist that competes with the protein for binding with the other member of the interaction (the other cellular component), leading to a decrease in the interaction and hence a decrease of the cellular activity controlled or caused (directly or indirectly) by the interaction. Where the cellular activity is an "on" physiological process, (for example, increase in production of an agent), the interruption will block the "on" reaction and decrease the physiological process (resulting in a decrease in the production of the agent). Where the cellular activity is an "off" reaction (for example a signal causing inhibition of proliferation), the interruption will block the "off" reaction and will increase the physiological process, for example, cause increased proliferation.

Alternatively, a drug may work as an agonist and cause the modulation of the cell activity by mimicking the protein (that is essential for the cell activity) in the interaction in such a manner that the cell activity takes place as if the native protein and not the compound were interacting with the other cellular component. For example the compound may be able to activate the cellular component with which the protein interacts in a similar way to the protein itself.

The aim of the compounds of the present invention is to mimic a region in one of the participators of the interaction, so as to compete for the binding on the other participator of the interaction (either in the antagonist or the agonist manner), thus changing the interaction and leading to a change in the physiological process or property controlled by the interaction.

The rationale for the present invention is the following: many libraries used for the discovery of drug leads are composed of heterocyclic scaffolds that are too constrained (rigid) to allow conformational complementarity essential for the interactions with proteins, peptides, polysaccharides or nucleic acids. The combinatorial library of the invention allows the generation of sub-libraries with spatial diversity, which is obtained by the diversity in ring size and chirality of the link between the substituent and the ring backbone or by combinations thereof. This results in a library where each individual member has a different flexibility and a different spatial positioning of the pharmacophore. The design of the library of the invention increases the probability that some members of the library have the ability to undergo conformational complementarily, i.e. the pharmacophores are present in the correct orientation to interrupt or mimic the interaction with the other cellular component. The present invention allows the design and synthesis of libraries, which occupy a larger proportion of the "probability space" of the pharmacophore positioning (i.e. increase the probability of the substituents to be present in varying positions in the space, thus increasing the probability that at least one positioning-conformation is the bioactive conformation), while still creating relatively small, focused libraries. These properties lead to fast discovery and optimization of novel drug leads.

The classical elements of diversity of state-of-the-art, currently available macrocyclic, i.e. scaffold based libraries are based mainly on:
(1) The chemical nature of the scaffold (i.e. backbone);
(2) The size and chemical nature of the linkers that connect between the backbone and the various substituents;
(3) The chemical nature of the substituents; and
(4) The order in which the substituents are arranged on the ring.

The libraries of the new compounds of the present invention comprise a novel element of diversity, namely spatial diversity, that results from (a) the varying size of the ring, (b), the chirality of the linker; or (c) or a combination of the two. This diversity is new in the field of small molecule combinatorial chemistry. In a preferred embodiment of the present invention, each member of the library differs from the other by the size of the ring. In another preferred embodiment, each member of the library differs from the other by the chirality of the substituents on the ring. Also encompassed within the scope of the present invention are libraries wherein each member differs from the other by both the size of the ring and the chirality of the substituent of the ring. Furthermore, the members of the library may further differ from one another by the "conventional" elements of diversity (1-4 defined hereinabove), i.e. by at least one parameter selected from: the chemical nature of the ring, the substituents on the ring, the linkers connecting the substituents and the ring, the arrangement of the substituents on the ring, or any combination thereof.

Spatial diversity is defined as diversity elements that alter the conformation of the compounds, which in fact lead to altered spatial positioning of the pharmacophore or pharmacophores.

According to one specific embodiment of the present invention, the members in a library share at least some of the elements defined in items (1)-(4) mentioned above: the same type of scaffold backbone with the same composition of atoms within the ring; the same linker with the same size and chemical nature; the same substituents arranged in the same order on the ring, but they differ from each other in the size of the scaffold and/or the chirality of the linker. This in turn determines the possible conformational (spatial) positioning of the pharmacophore of each compound and allows for the selection of the lead compound having the appropriate ability of conformational complementarity. The libraries of the invention are composed of a series of compounds that differ from each other by an incremental alteration of their possible conformations. Thus, every library covers an entire range of the conformational probabilities and increases the chances of obtaining a compound with at least one bioactive conformation.

A "lead compound" is a library compound in a selected combinatorial library, for which the assay has revealed significant effect relevant to a desired cell activity to be modulated. In the present case the property is the modulation of at least one biological activity associated with a cellular component which the library compound either interacts with or mimics.

The selection of an active candidate is preferably achieved from a library of compounds that have the same substituents in different positions along the ring but the rings differ from each other in size and chirality of the substituents and therefore in their conformation. The libraries are prepared by the multiple simultaneous solid phase method [Houghten R. A., 1985] or its automated version, and contain the calculated number of diversity possibilities. Libraries are typically synthesized in a 12-48 format, namely each library typically contains 12-48 members. Each member of the library will be characterized, purified and subjected to biological assay.

The pharmacophore has proven to be a highly valuable and useful concept in drug discovery and drug-lead optimization. A pharmacophore is defined as a distinct three dimensional (3D) arrangement of chemical groups essential for biological activity. Since a pharmaceutically active molecule must interact with one or more molecular structures within the body of the subject in order to be effective, and the desired functional properties of the molecule are derived from these interactions, each active compound must contain a distinct arrangement of chemical groups which enable this interaction to occur. The chemical groups, commonly termed descriptor centers, can be represented by (a) an atom or group of atoms; (b) pseudo-atoms, for example a center of a ring, or the center of mass of a molecule; (c) vectors, for example atomic pairs, electron lone pair directions, or the normal to a plane. Clearly, the ability to design, or identify from large databases, pharmaceutically useful molecules according to the pharmacophore would be highly effective both in the process of drug discovery and in to the process of drug lead optimization.

In the present invention the term refers to those moieties of the side chain or backbone of the cellular components, for example peptide, protein or nucleic acid (which mediate a cell activity), that are necessary for the binding to the other cellular components, the binding eliciting a biological response. The pharmacophore may be a chemical moiety present on a single side chain or a collection of chemical moieties present in spatially adjacent side chains.

Novel Compound

Thus, in one embodiment, the present invention provides a heterocyclic compound represented by the structure of formula I.

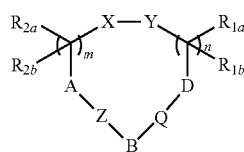

wherein

A, B and D are independently of each other $CH_2$, $C=O$ or a bond;

X and Y are independently of each other O, S, $C=O$, $S=O$, $SO_2$, $CR_{3a}R_{3b}$, $NR_4$ or $C=S$, or X and Y together form a group represented by the formula:

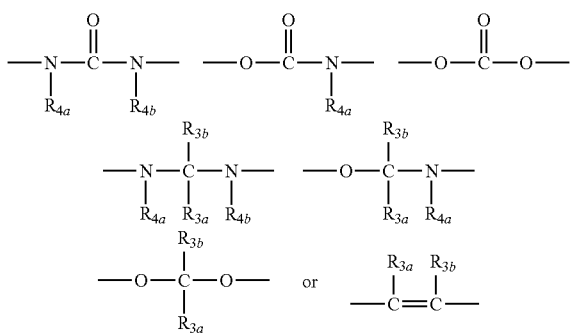

$R_{1a}$, $R_{1b}$, $R_{2a}$, $R_{2b}$, $R_{3a}$, $R_{3b}$, $R_{4a}$ and $R_{4b}$ are independently of each other hydrogen or a linear or branched chain alkyl;

m and n are independently of each other an integer of 1-6;

Z and Q are independently of each other

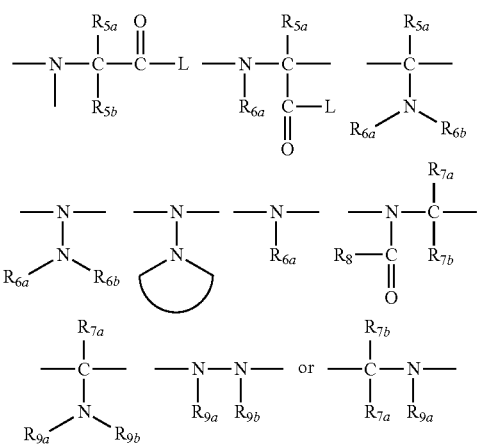

$R_{5a}$, $R_{5b}$, $R_{6a}$, $R_{6b}$, $R_{7a}$, $R_{7b}$, $R_8$, $R_{9a}$, and $R_{9b}$ are independently of each other hydrogen, a linear or branched chain alkyl, cycloalkyl, aryl, aralkyl, heterocyclyl, heteroaryl, acyl, carboxyalkyl, carboxyaryl, benzyl, hydroxybenzyl, benzyloxycarbonyl, a side chain of a natural or unnatural amino acid or a peptide;

L is hydrogen, $OR_{10}$, or $NHR_{11}$ wherein $R_{10}$ and $R_{11}$ are independently of each other hydrogen, a linear or branched chain alkyl, a side chain of a natural or unnatural amino acid, a peptide or a solid support; and

is a heterocyclic moiety containing one or more nitrogens;

or a pharmaceutically acceptable salt, hydrate or solvate thereof.

In one embodiment, the present invention provides a compound of formula I wherein A and D are a bond and B is $C=O$. In another embodiment, the present invention provides a compound of formula I wherein A is a bond, B is $CH_2$ are C is $C=O$.

In another embodiment, the present invention provides a compound of formula I wherein Q is

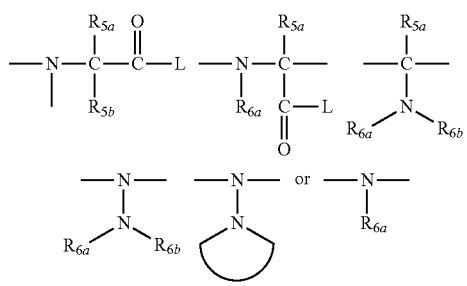

In another embodiment, the present invention provides a compound of formula I wherein Z is

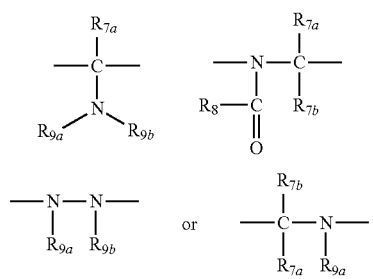

In another embodiment, the present invention provides a compound of formula I wherein one of $R_{5a}$ and $R_{5b}$ is hydrogen and the other is benzyl. In another embodiment, the present invention provides a compound of formula I wherein one of $R_{5a}$ and $R_{5b}$ is hydrogen and the other is hydroxybenzyl. In another embodiment, the present invention provides a compound of formula I wherein one of $R_{6a}$ and $R_{6b}$ is hydrogen and the other is benzyl. In another embodiment, the present invention provides a compound of formula I wherein one of $R_{6a}$ and $R_{6b}$ is hydrogen and the other is hydroxybenzyl. In another embodiment, the present invention provides a compound of formula I wherein one of $R_{7a}$ and $R_{7b}$ is hydrogen and the other is benzyl. In another embodiment, the present invention provides a compound of formula I wherein one of $R_{7a}$ and $R_{7b}$ is hydrogen and the other is hydroxybenzyl. In another embodiment, the present invention provides a compound of formula I wherein $R_8$ is benzyloxycarbonyl. In another embodiment, the present invention provides a compound of formula I wherein one of $R_{9a}$ and $R_{9b}$ is hydrogen and the other is benzyloxycarbonyl. In another embodiment, the present invention provides a compound of formula I wherein L is $NH_2$.

In another embodiment, the present invention provides a heterocyclic compound to represented by the structure of any of formulas II-X.

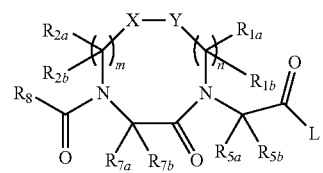
II

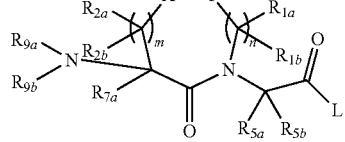
III

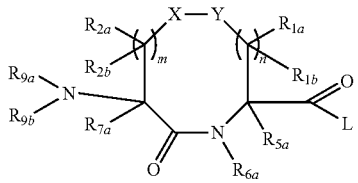
IV

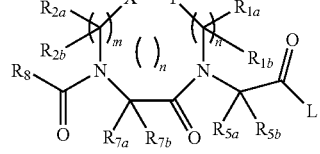
V

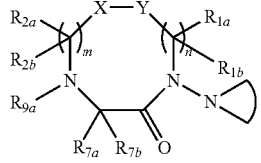
VI

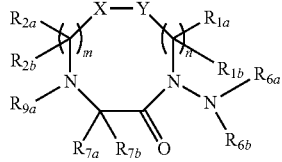
VII

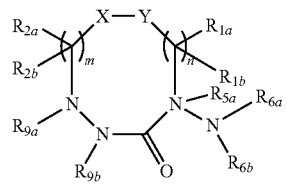
VIII

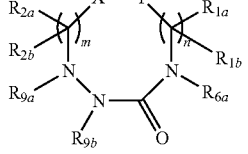
IX

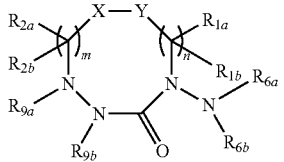
X

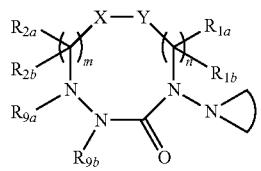
XI

In one embodiment, the present invention provides a compound of formula II.

In another embodiment, the present invention provides a compound of formula III.

In another embodiment, the present invention provides a compound of formula IV.

In another embodiment, the present invention provides a compound of formula V.

In another embodiment, the present invention provides a compound of formula VI.

In another embodiment, the present invention provides a compound of formula VII.

In another embodiment, the present invention provides a compound of formula VIII.

In another embodiment, the present invention provides a compound of formula IX.

In another embodiment, the present invention provides a compound of formula X.

In another embodiment, the present invention provides a compound of formula XI.

As contemplated herein, the following definitions are used herein to describe the compounds of the present invention:

The term "substituent" refers to a chemical radical or functional group which is bonded to or incorporated onto the ring during the synthetic process used to generate the library. The different functional groups are typically selected based on the knowledge concerning the pharmacophore that possesses a desired structure, function and biological activity The term "alkyl" refers to a straight or branched chain or cyclic hydrocarbon having 1-12 carbon atoms. In one embodiment, the alkyl has 1-10 carbons. In another embodiment, the alkyl has 1-8 carbons. In another embodiment, the alkyl has 1-6 carbons. In another embodiment, the alkyl has 14 carbons. The alkyl may be unsubstituted or by one or more inert substituents, i.e. substituents which do not interfere with the biological activity or conformational flexibility of the compounds. Non-limiting examples of suitable inert substituents are but are not limited to halo, hydroxy, $C_1$-$C_{10}$ alkyl, $C_2$-$C_{10}$ alkenyl, $C_2$-$C_{10}$ alkynyl, $C_1$-$C_{10}$ alkoxy, $C_7$-$C_{12}$ aralkyl, $C_7$-$C_{12}$ alkaryl, $C_1$-$C_{10}$ alkylthio, arylthio, aryloxy, arylamino, $C_3$-$C_{10}$ cycloalkyl, $C_3$-$C_{10}$ cycloalkenyl, di($C_1$-$C_{10}$)-alkylamino, $C_{2-12}$ alkoxyalkyl, $C_1$-$C_6$ alkylsulfinyl, $C_1$-$C_{10}$ alkylsulfonyl, arylsulfonyl, aryl, hydroxy, hydroxy($C_1$-$C_{10}$)alkyl, aryloxy($C_1$-$C_{10}$)alkyl, $C_1$-$C_{10}$ alkoxycarbonyl, aryloxycarbonyl, acryloyloxy, substituted alkoxy, fluoroalkyl, nitro, cyano, cyano($C_1$-$C_{10}$)alkyl, $C_1$-$C_{10}$ alkanamido, aryloylamido, arylaminosulfonyl, sulfonamido, amidino, amido, alkylamido, dialkylamido, amino, alkylamino, dialkylamino, carbonyl, carbamido, carboxy, heterocyclic radical, nitroalkyl, and —$(CH_2)_m$—Z—($C_1$-$C_{10}$ alkyl), where m is 1 to 8 and z is oxygen or sulfur.

The term "aryl" refers to an aromatic group having at least one carbocyclic aromatic group, which may be unsubstituted or substituted by one or more inert substituents as defined hereinabove.

The term "heterocyclyl" or "heteroaryl" refers to a ring containing one or more heteroatoms, for example oxygen, nitrogen, sulfur and the like, with or without unsaturation or aromatic character, optionally substituted with one or more inert substituents as defined hereinabove. Non-limiting examples of heterocyclic substituents are imidazole, pyrazole, pyrazine, thiazole, thiazine, oxazole, furan, dihydrofuran, tetrahydrofuran, pyridine, dihydropyridine, tetrahydropyridine, isoxazole and the like. Multiple rings may be fused, as in quinoline or benzofuran, or unfused as in 4-phenylpyridine.

The heterocyclic moiety

is a heterocyclic moiety containing one or more nitrogens, which may be isolated or fused, for example and without being limited to -imidazole, pyrazole, pyrazine, pyridine, dihydropyridine, tetrahydropyridine, isoxazole, quinoline, isoquinoline and the like.

A "haloalkyl" group refers to an alkyl group as defined above, which is to substituted by one or more halogen atoms, e.g. by F, Cl, Br or I. A "hydroxyl" group refers to an OH group. An "alkenyl" group refers to a group having at least one carbon to carbon double bond. A halo group refers to F, Cl, Br or I. An "arylalkyl" group refers to an alkyl bound to an aryl, wherein alkyl and aryl are as defined above. An example of an arylalkyl group is a benzyl group.

The term "solid support" refers to a solvent insoluble material having cleavable covalent bonds for use in preparing the library compounds of the invention.

As contemplated herein, the present invention further encompasses analogs, derivatives, isomers, pharmaceutically acceptable salts and hydrates of the heterocyclic compounds defined by the present invention.

The term "isomer" includes, but is not limited to, optical isomers and analogs, structural isomers and analogs, conformational isomers and analogs, and the like. In one embodiment, this invention encompasses of various optical isomers of the compounds of the present invention. It will be appreciated by those skilled in the art that the compounds of the present invention contain at least one chiral center. Accordingly, the these compounds exist in, and be isolated in, optically-active or racemic forms. Some compounds may also exhibit polymorphism. It is to be understood that the present invention encompasses any racemic, optically-active, polymorphic, or stereroisomeric form, or mixtures thereof. In one embodiment, the compounds the pure (R)-isomers. In another embodiment, the compounds are the pure (S)-isomers. In another embodiment, the compounds are a mixture of the (R) and the (S) isomers. In another embodiment, the compounds are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes pharmaceutically acceptable salts of the heterocyclic compounds of the present invention. Pharmaceutically acceptable salts can be prepared by treatment with inorganic bases, for example, sodium hydroxide or inorganic/organic acids such as hydrochloric acid, citric acids and the like.

This invention further includes derivatives of the compounds. The term "derivatives" includes but is not limited to ether derivatives, acid derivatives, amide derivatives, ester derivatives and the like. In addition, this invention further includes hydrates of the compounds described herein. The term "hydrate" includes but is not limited to hemihydrate, monohydrate, dihydrate, trihydrate and the like.

Combinatorial Libraries

The invention also provides, according to another of its embodiments, a combinatorial library comprising a plurality of heterocyclic compounds having a ring size of between 8-20 atoms wherein the members of the library differ from each other in the size of the ring, the chirality of the substituents on the ring or a combination of the two. In further preferred embodiments the members of the library are distinct from one another in the nature, number, positioning, of substituents along the ring, or in the nature and chirality of the linking moieties that join the substituents to the ring.

Currently more preferred compounds according to the present invention are represented by the structure of any of formulas I-X. A "library" is a collection of compounds which, while sharing some common structural elements (which may be common scaffolds, common ring sizes, common substituents and the like), are diverse from each other by at least one of the following properties: i) the size of the ring; ii) the order in which the pharmacophores are arranged in the ring; iii) the chemical nature of the ring; iv) the chemical nature of the pharmacophores; v) the chirality of the linker between the ring and the pharmacophore; and vi) the chirality of the pharmacophore. The library allows screening from among a plurality of compounds for those that have a desired property. The library may be designed by a combinatorial or classical chemical process.

In one embodiment, the library comprises at least one compound represented by the structure of formula I. In another embodiment, the library comprises at least one compound represented by the structure of formula II. In another embodiment the library comprises at least one compound represented by the structure of formula III. In another embodiment, the library comprises at least one compound represented by the structure of formula IV. In another embodiment, the library comprises at least one compound represented by the structure of formula V. In another embodiment, the library comprises at least one compound represented by the structure of formula VI. In another embodiment, the library comprises at least one compound represented by the structure of formula VII. In another embodiment, the library comprises at least one compound represented by the structure of formula VIII. In another embodiment, the library comprises at least one compound represented by the structure of formula IX. In another embodiment, the library comprises at least one compound represented by the structure of formula X.

In a preferred embodiment of the present invention, each member of the library differs from the other by the size of the ring. In another preferred embodiment, each member of the library differs from the other by the chirality of the substituents on the ring. In another embodiment, each member of the library differs from the other by at least one of the size of the ring or the chirality of the substitutents of the ring; and further differs by at least one of the chemical nature of the ring, the substituents on the ring, the linkers connecting the substituents and the ring, the arrangement of the substituents on the ring, or any combination thereof.

The combinatorial libraries of the invention serve as a readily accessible source of diverse macrocyclic compounds for use in identifying new biologically active macrocyclic compounds through pharmaceutical and veterinary candidate screening assays, for the development of highly effective and environmentally friendly insect control and crop control agents, for use in studies defining structure/activity relationships, and/or for use in clinical investigation.

Design of Libraries and Identification of Biologically Active Compounds

Furthermore, in another embodiment, the present invention provides methods for designing new compound libraries that have a novel type of structural complexity and diversity, and that can be screened to identify potent compounds for pharmaceutical, veterinary or agricultural use. Molecules having a molecular weight of up to about 1000 daltons, i.e. small molecules, are preferable.

Thus, in one embodiment the present invention provides a method of identifying a compound having a beneficial biological activity, by (a) designing a combinatorial library comprising a plurality of heterocyclic compounds having a ring size of between 8 to 20 atoms wherein some members of the library differ from others in at least one aspect selected from the ring size; and the chirality of the substituents on the ring, wherein each member of the library comprises at least one pharmacophore potentially associated with the biological activity; (b) synthesizing a plurality of compounds from the combinatorial library; and (c) screening the synthesized compounds for candidates having the desired biological activity.

In one embodiment, between step (a), i.e. planning the combinatorial library, and step (b) i.e. synthesizing the compounds of the library, it is possible to add a step of virtually screening the library to identify those compounds which most closely resemble or fit the pharmacophore that interacts with a domain in the cellular component and is associated with the desired biological activity. Such virtual screening can help and predict which compounds have a better chance of assuming the bioactive conformation and it is preferable to start the screening with the compounds that are, according to 3D modeling the most likely mimics/docking compounds. Thus, in one embodiment, the method further comprises the following steps as part of the designing step (a): (a1) identifying a domain in a cellular component which is associated with the biological activity; and (a2) virtually screening the combinatorial library for lead compounds having a pharmacophore complementary to or capable of mimicking the domain. In one embodiment, the virtual screening step comprises virtual screening of the library with a computer readable data storage material encoded with computer readable data comprising three-dimensional structural determinants defining the desired domain. In yet another aspect, the computer readable data storage material is further encoded with a computer program logic for controlling a processor, wherein the computer program logic comprising a procedure that enables the processor to identify a member of the combinatorial library having a pharmacophore complementary to the desired domain domain. The above steps are showed schematically in the following chart:

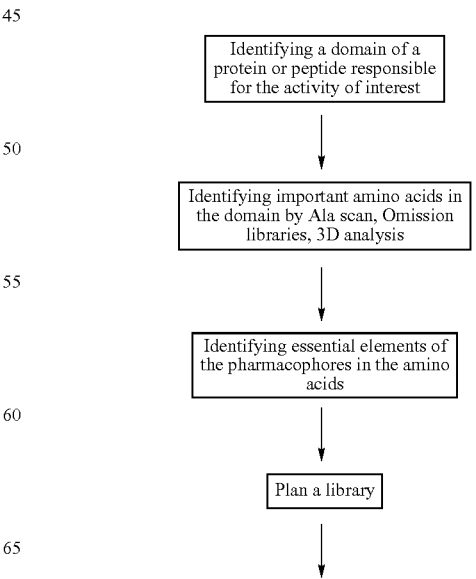

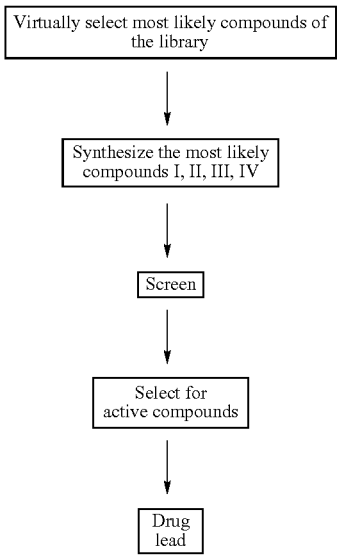

As the compounds of the invention are intended to mimic or to bind to a domain in a cellular component, for example a protein or a nucleic acid, so as to interrupt or to mimic its interaction with other cellular components and thus modulate the biological activity (mediated by the cellular component), it is desired that they resemble the desired domain structurally and spatially as closely as possible. Therefore, when deciding at the library planning step how to produce the best library, and at the synthesizing step, which of the members of the planned library should be synthesized, the following questions should be asked:
1. Are the relevant pharmacophores (or derivatives or mimics of the pharmacophores) present in the planned library?
2. Is the order of the substituents on the ring and the distance of the substituents from each other, suitable for achieving a suitable bioactive conformation (correct positioning of the pharmacophores)?
3. Is the compound capable in one of its conformations of attaining the correct positioning of the pharmacophores?
4. Is the possible conformation energetically favorable?
5. Is there a certain degree of conformation flexibility to allow conformational complementarity?

Most of the above questions can be answered during the planning stage and the synthesis decision stage on a computer using commercially available bioinformatic programs such as Tripose™.

The coordinates of amino acid side chains of a protein can be obtained from the Protein Data Bank (PDB) files. This data is based on the 3D structure of the protein (preferably as a complex with the appropriate ligand) either obtained by crystallography or homology modeling. The 3D information allows to identify the exposed side chains and these accessible side chains are possible pharmacophores. In cases of proteins for which the 3D structure was not determined, the essential amino acids within a protein may be determined by the method of combinatorial alanine-scanning (Morrison and Weiss, (2001)), also known as Ala-Scan. Another method is known as omission libraries and is described in Campian et al. (1998). Yet other methods are site directed mutagenesis and protein engineering (Winter et al (1982)). The amino acids and backbone elements essential for a certain function may be divided into two categories: those who interact with the receptive protein, nucleic acid, polysaccharide or cell membrane and those responsible for the conformation of the essential region. The side chains and backbone elements of the former are those that participate in the creation of pharmacophores and the present invention relates to the creation of such pharmacophores, or their mimics and their incorporation in the scaffolds of the invention for the purpose of creating a mimic of a region of the protein.

As mentioned above, the essential amino acids within a protein may be determined by the method of combinatorial alanine-scanning. Alanine scanning, a method of systematic and sequential alanine substitution, has been particularly useful for the identification of pharmacophores in a given peptide sequence. This method is based on the synthesis of a library in which each amino acid residue in a peptide chain is sequentially replaced by alanine, and biological screening of the library. Substitution of functional amino acid residues by the methyl group of alanine leads to the removal of all the side chain atoms past the β-carbon. Thus, the role of side-chain functional groups at specific position can be inferred. Alanine residue have the same backbone dihedral angles as other functional residues and thus the backbone conformation is not drastically perturbed by such substitution, as would be the case in glycine scan libraries. In this case, the side chain is nullified, which leads to the introduction of flexibility into the peptide backbone.

An additional method for the elucidation of pharmacophores is the synthesis and biological screening of omission libraries. Omission libraries, based on a given peptide sequence is a library that contain all the possible peptides that compose the parent peptide. Omission library is divided into sequential and non sequential. In sequential omission library, amino acids are omitted from the carboxy- and amino-ends, whereas in non sequential library amino acids are omitted from the interior of the peptide sequence. Thus, sequential omission library based on a hexapeptide contains 2 pentapeptides, 3 tetrapeptides, 4 tripeptides and 5 dipeptides (total of 14 peptides). Non-sequential omission library based on a hexapeptide contains 4 pentapeptides, 18 tetrapeptides, 27 tripeptides and 9 dipeptides (total of 58 peptides). Beside information on essential pharmacophores, omission libraries can furnish shorter active peptides that will facilitate the design of libraries.

In conclusion, the method of the invention utilizes spatial libraries that can generate novel leads for the disruption of protein:protein, protein:peptide, protein:cell membrane and protein:nucleic acid interactions, in animals and plants.

Computer Automation

As contemplated herein, any of the methods provided by the present invention may to be adapted for high-throughput by computer automation. Thus, the present invention provides computer program products virtual screening of the combinatorial library of heterocyclic compounds provided herein for a compound having a beneficial biological activity. The computer program product according to one embodiment of the present invention comprises (a) a computer readable data storage material encoded with computer readable data comprising three-dimensional structural determinants defining a domain in a cellular component which is associated with the desired biological activity, and (b) a computer program logic for controlling a processor, comprising a procedure that enables the processor to identify a compound having a pharmacophore complementary to the desired domain.

Furthermore, in yet another embodiment, the present invention provides a system for identifying a compound having a beneficial biological, comprising: (a) an automated device for virtual screening of the combinatorial library of heterocyclic compounds provided herein for a compound having said beneficial biological activity; and (b) an experimental device for screening these compounds for candidates having the desired biological activity.

In one embodiment, the automated device comprises the computer program product described hereinabove. In another embodiment, the experimental device comprises (a) an apparatus for synthesizing the compounds identified in step (a); and (b) an apparatus for experimentally screening the compounds for candidates having the desired biological activity.

Pharmaceutical Compositions and Therapeutic Uses

In one embodiment, the compounds defined by the present invention are useful in the treatment of a disease, disorder or condition. In another embodiment, therapy of the disease, disorder or condition is achieved by modulation of a cellular component, for example a protein, a nucleic acid or a combination thereof. The compounds provided herein, either alone or in the pharmaceutical compositions are suitable for use in any subject, for example a mammalian subject or a human subject. The pharmaceutical compositions of the present invention are also suitable for use in veterinary medicine and furthermore may be used in agriculture.

Furthermore, in another embodiment, the present invention provides a pharmaceutical composition comprising at least one heterocyclic compound as defined hereinabove, and a pharmaceutically acceptable carrier. Furthermore, in yet another embodiment, the present invention provides a method for the treatment of a disease, condition or disorder in a subject in need thereof, comprising the step of administering to the subject a therapeutically effective amount of a heterocyclic compound provided by the present invention.

The term "therapeutically effective amount" as used herein refers to that amount which provides a therapeutic effect for a given condition and administration regimen. For example this term may refer to an amount capable of decreasing, to a measurable effect, at least one adverse manifestation of the disease and should be chosen in accordance with the drug used, the mode of administration, the age and weight of the patient, the severity of the disease, etc.

A "biological activity associated with a cellular component" refers to a physiological property of a cell that is caused, directly or indirectly (the latter referring to an effect caused by an effector which is more downstream in the pathway) by the interaction between one cellular component to another (the term "cellular component" including: other proteins or peptides of the same or different types, membranes, nucleic acids, lipoproteins, nucleotides, co-factors, hormones, ion effectors and the like). The interaction between cellular components may be of the type: receptor-ligand, enzyme-substrate, antigen-antibody, DNA-binding proteins—DNA etc. Said interaction mediates (causes) directly or indirectly, a biological activity such as: expression of a protein, proliferation, differentiation, cell-elongation, cell-shape alteration, cellular metabolism, cellular uptake of external substances, secretion of substances from the cells and the like.

"Modulate/Modulator" refers to increase or decrease in at least biological activity associated with a cellular component, in the presence of the compound of the invention, or to the change of the response of the cell to the presence of a physiological cue, as compared to the activity or response, respectively, in the absence of the compound. Examples of such physiological cues are presence of effectors, the modulation being a change in the cellular response to a ligand, hormone, response to toxic substances (pesticides), stress (heat shock, draught, lack of nutrients) aging and the like.

As contemplated herein, non-limiting examples of the desired biological activity is proliferation, differentiation, phenotype alteration, uptake of external substances into cells, secretion of substances from cells, metabolism, gene expression, protein expression, or any combination thereof.

In accordance with another embodiment of the invention, the compounds of the invention may be bound to a detectable label such as a fluorescence-emitting moiety, a radio-label, a label capable of undergoing an enzymatic reaction producing a detectable color, a marker for x-ray, MRI, radio-isotope imaging or PET scan, to produce a labeled adduct. Then, upon administration of such labeled adduct, it may be detected at a desired location by any manner known in the art and in accordance with the specific label used, for example, fluorescence, radioactive emission, or a color production, MRI, x-ray and the like.

The term "bound" refers to covalent or non-covalent (e.g., electrostatic) binding, which connects the compound of the invention to the detectable label. Alternatively, the compound of the invention may have inherent detectable properties of its own, that enable it to be detected by any of the above mentioned techniques.

The pharmaceutical composition of the invention may be administered by any of the known administration routes, inter alia, oral, intravenous, intraperitoneal, intramuscular, subcutaneous, sublingual, intraocular, intranasal or topical administration routes. Appropriate unit dosage forms of administration include the forms for oral administration, such as tablets, capsules, powders, granulates and oral solutions or suspensions and the forms for sublingual and buccal administration, the forms for parenteral administration useful for a subcutaneous, intramuscular or intravenous injection, as well as the forms for rectal administration.

The carrier should be selected in accordance with the desired mode of administration and include any known components, e.g. solvents; emulgators, excipients, talc; flavors; colors, etc. The pharmaceutical composition may comprise, if desired, also other pharmaceutically-active compounds which are used to treat the disease, eliminate side effects or augment the activity of the active component.

In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Typically, the pharmaceutical compositions of this invention will be administered from about 1 to about 5 times per day or alternatively, as a continuous infusion. A typical preparation will contain from about 5% to about 95% active compound (w1w). Preferably, such preparations contain from about 20% to about 80% active compound. As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration; rate of excretion, drug combination, the patient's disposition to the disease state and the judgment of the treating physician. In general, the compound is most desirably administered at a concentration level that will generally afford effective results without causing any harmful or deleterious side effects.

The pharmaceutical composition may comprise, if desired, also other pharmaceutically-active compounds which are used to treat the disease, eliminate side effects or augment the activity of the active component.

Synthetic Approach

In general, the compounds of the invention are prepared according to the routes showed in Schemes 1-4 below. The solid phase synthesis of scaffolds I-IV comprise of a series of couplings of the appropriate protected acids and reductive alkylations with ω-functionalized protected aldehydes. The assembly of the appropriate linear scaffold on the solid support is followed by removal of the protecting groups $P_1$ and $P_2$ and cyclization. The appropriate scaffold is obtained after deprotection-removal from the solid support.

Scheme 1: General solid phase synthesis of libraries of scaffold I

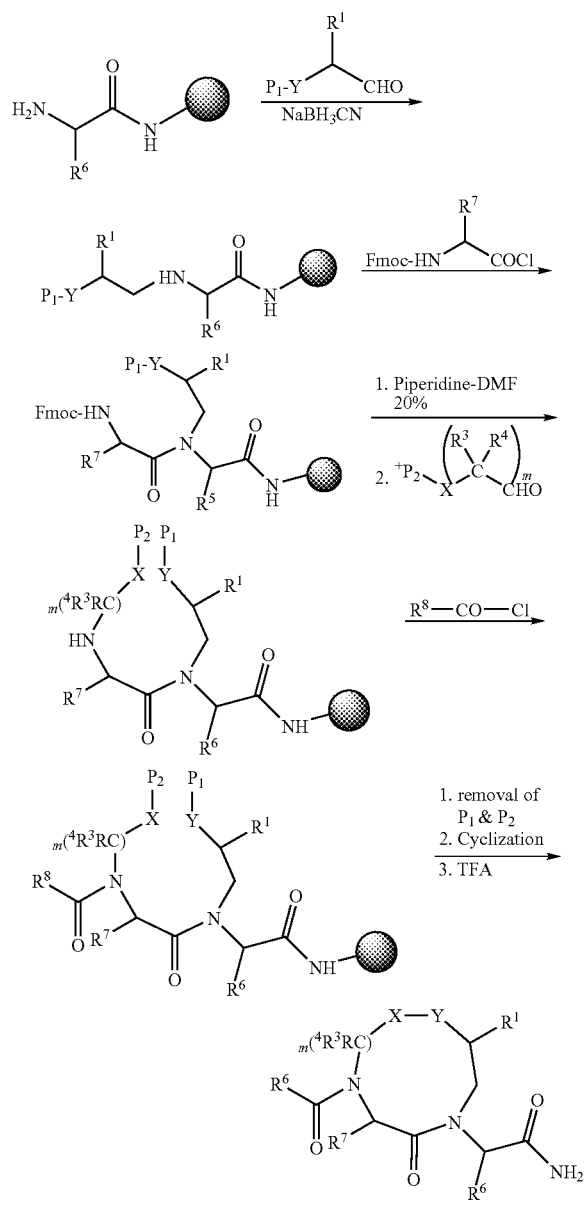

Scaffold I $P_1$ and $P_2$ are orthogonal protecting groups on Y and X respectivly
$R^2 = H; L = NH_2; n = 2$ Scheme 2: General solid phase synthesis of libraries of scaffold II

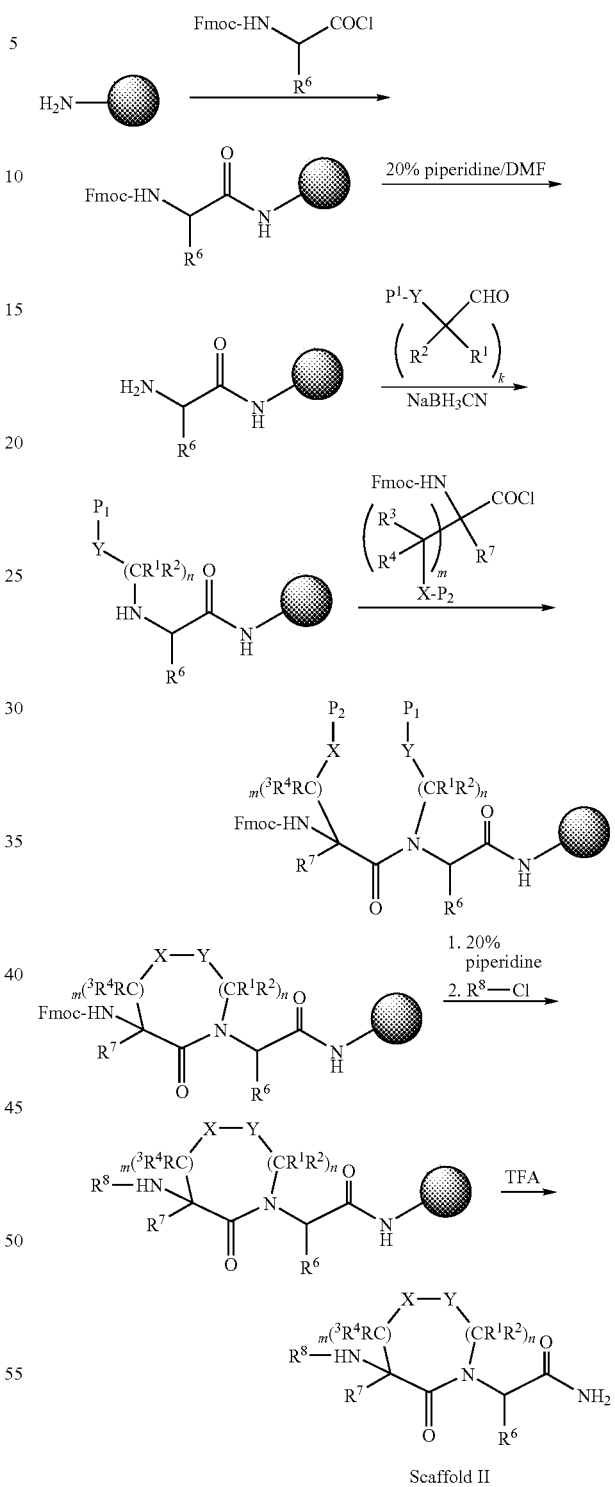

Scaffold II $P_1$ and $P_2$ are orthogonal protecting groups on Y and X respectivly Scheme 3: General solid phase synthesis of libraries of scaffold III

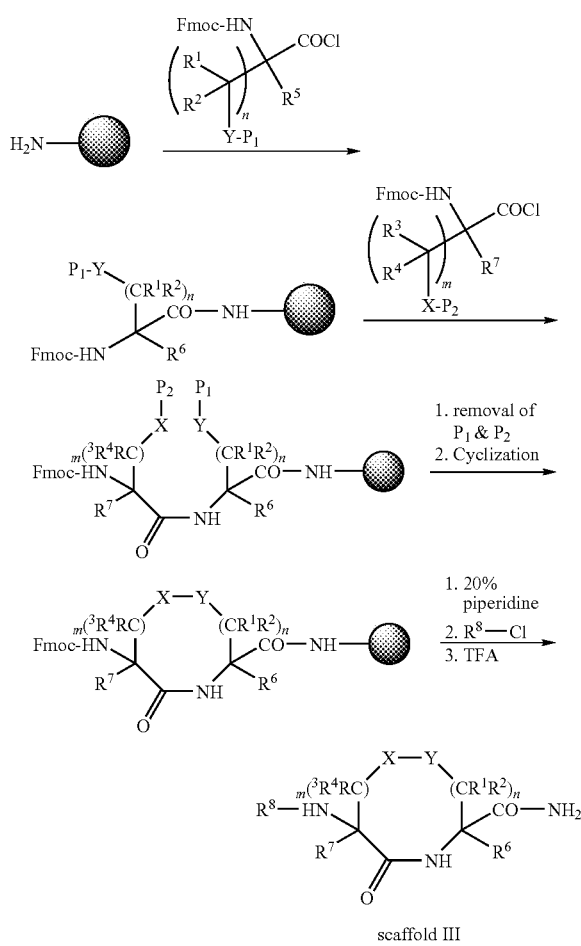

scaffold III $P_1$ and $P_2$ are orthogonal protecting groups on Y and X respectivly Scheme 4: General solid phase synthesis of libraries of scaffold IV

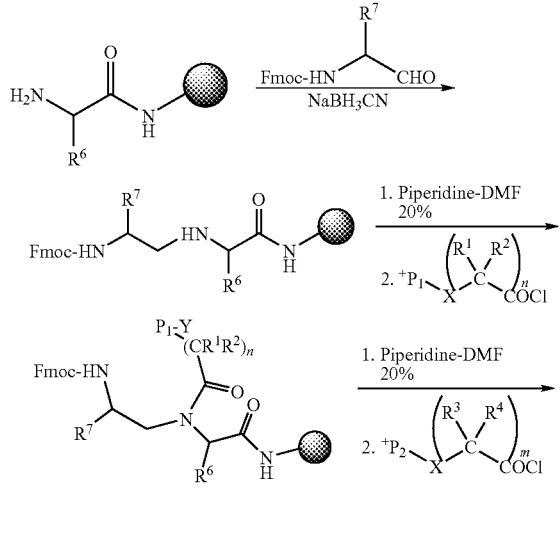

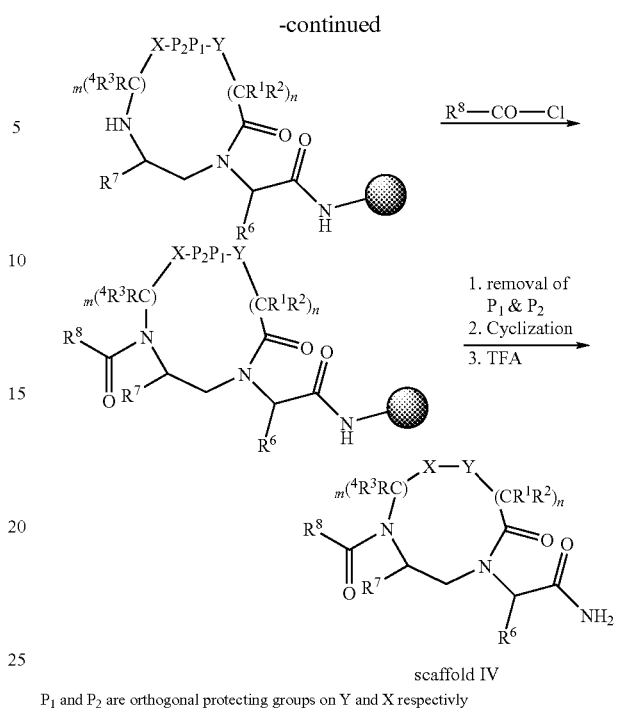

scaffold IV $P_1$ and $P_2$ are orthogonal protecting groups on Y and X respectivly
$R^5 = H; L = NH_2$ The following examples are presented in order to more fully illustrate the preferred embodiments of the invention. They should in no way, however, be construed as limiting the broad scope of the invention.

EXPERIMENTAL DETAILS SECTION

Example 1

Synthesis

A library composed of 26 molecules that have the formula I wherein $R^1$ and $R^2$ are either benzyl (side chain of phenylalanine) or hydroxybenzyl (side chain of tyrosine) and $R^3$ is benzyloxycarbonyl (which is a mimic of the side chain of phenylalanine) was synthesized and characterized. The library was synthesized by the Simultaneous Multiple Solid Phase methodology (Houghten (1985)) as showed in Scheme 5 below. The molecules were characterized by HPLC, MS and MS-MS spectrometry.

Scheme 5: Solid phase synthesis of a library of compounds according to the invention (for structures of $R^6$, $R^7$, $R^8$, m and n, see Table 1)

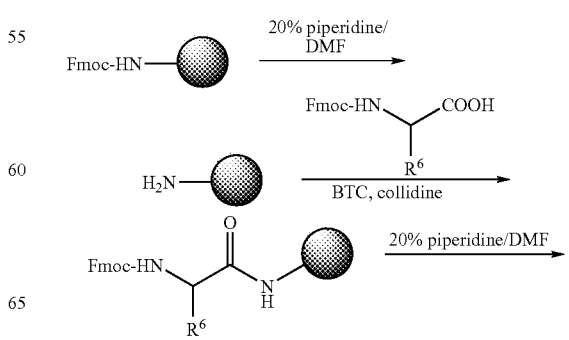

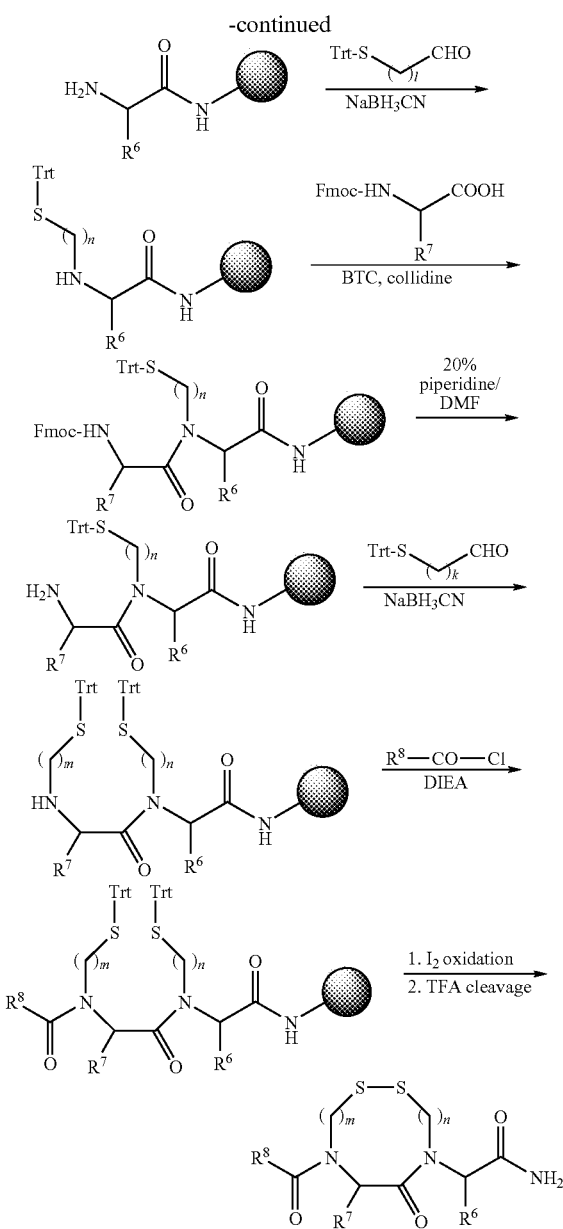

Synthetic Procedures According to Scheme 5 Above:

Rink amide MBHA resin [Rink H. (1987)] (0.1 g in each bag, 0.6 mmol/g) was pre-swollen for 2 h in NMP while shaking in reaction vessel equipped with sintered glass bottom. The Fmoc protecting group was removed from the resin by reaction with 20% piperidine in NMP (2×30 min). Fmoc removal was monitored by chloranil test. A coupling cycle was carried out with Fmoc-AA (AA is abbreviation of amino acid) (5 eq), BTC (1.65 eq), and 2,4,6 colidine (14 eq) in DCM for 2 h at room temperature. Reaction completion was monitored by qualitative chloranil test. Following coupling the peptidyl-resin was washed with DCM (×5) and for 2 min. Fmoc removal and washing steps were carried out as described above. Fmoc removal was monitored by the chloranil test.

The peptidyl-resin was then washed by a mixture of NMP: MeOH 1:1/1% and a solution of the aldehyde (1 eq) in the mixture above was added (10 ml for 12 bags). Then additional 40 ml of this mixture was added and the mixture was shaken for 5 min. Then, 2 eq of $NaBH_3CN$ were added and the reaction vessel was shaken for 2 h. The resin was washed as follows: DCM (2×2 min), EtOH (2×2 min), NMP (2×2 min), DCM (3×2 min). (Chloranil test gave blue color immediately). The following coupling was performed using Fmoc-AA (5 eq), BTC (1.65 eq) and 2, 4, 6 colidine (14 eq) in dibromomethane at 50° C. for 2 h and was repeated when necessary. Fmoc deprotection and washing steps were carried out as described above. Reductive alkylation and washing steps were carried out as described above. A solution of benzylchloroformate (6 eq), and DEA (12 eq) in DMF was added to the resin and the mixture was shaken for 1 h. The reaction was repeated and ten the resin was washed with NMP (5×2 min) and DCM (2×2 min). Reaction completion was monitored by chloranil test.

Disulfide Bridge Formation:

The disulfide bridge was oxidized using iodine (10 eq) in DCM and shaking for 3 h. The resin was washed as follows: DMF (2×2 min), 2% ascorbic acid in DMF (2×2 min), NMP (5×2 min), DCM (4×2 min).

Analytical Procedures:

All the crude compounds were analyzed by MS and analytical reversed-phase HPLC (RP18 Vydak 4×250 mm; flow: 1 mL/min; T=30° C.; detection UV 214 nm; gradient: A=0.1% TFA in TDW, B=0.1% TFA in $CH_3CN$, 0 min 95:5, 5 min 95:5, 33 min 5:95, 38 min 95:5, 42 min 95:5).

The molecules were purified by preparative reversed-phase HPLC (RP18 Vydak 2.5×50 mm; flow: 9 mL/min; T=30° C.; detection UV 214 nm; gradient: A=0.1% TFA in TDW, B=0.1% TFA in $CH_3CN$, 0 min 95:5, 5 min 95:5, 33 min 5:95, 38 min 95:5, 42 min 95:5).

Fractions were collected, lyophilized and characterized by analytical HPLC and MS analysis. Results are shown in Table 1 below.

Synthesis of Aldehydes

Trityl Thiopropanal:

(a)) Trityl-Thiopropanoic Acid

Trityl mercaptan (36.13 g, 0.131 mol) was added stepwise to a suspension of NaH (11.5 g, 60% in mineral oil 0.288 mol) in 80 mL DMF under cooling and nitrogen atmosphere, the reaction mixture was stirred 30 minutes after the addition was completed. Then, a solution of bromopropionic acid (20 g, 0.131 mol) dissolved in 50 mL DMF was added stepwise. After the addition was completed the reaction mixture was stirred for 30 minutes and then cooling and nitrogen atmosphere were stopped and the reaction mixture was sealed and left overnight. Then, 500 mL chloroform were added and the mixture was washed with 4×200 mL of saturated solution of $KHSO_4$ and 4×200 mL TDW (the solid that precipitate during the washings should also be collected with the organic layer). The organic layer was evaporated and the product (that contained DMF traces) was precipitated by adding 300 mL TDW and stirring for few minutes. The product was collected by filtration and dried by suction and then in vacuo. The crude product was purified as follows: 150 mL of $CHCl_3$ were added to the white solid and the mixture was stirred for few minutes. Then 200 mL of PE 40-60 were added and the solid was collected by filtration yielding 37.61 g (82% yield) of white powder, mp 177-183° C., $^1$H NMR ($CDCl_3$, 300 MHz, 298K) δ 2.24 (t, 2H), 2.46 (t, 2H), 7.18-7.48 (m, 15H). MS (ES) m/z 347.

(b)) Trityl-Thiopropanoic Acid Hydroxamate

A solution of N,O dimethylhydroxylamine hydrochloride (2.188 g, 0.0225 mol) in 40 mL DMF was added to a mixture of 6.96 g (0.02 mol) of Trityl-thiopropanoic acid and PyBoP (11.45 g, 0.022 mol). DIEA (10.4 mL, 0.06 mol) was added and the clear solution was stirred for 3 hours. EA (120 mL)

was added to the stirred solution followed by 240 mL of saturated bicarbonate solution. The organic layer was collected and washed with additional two portions of 100 mL of saturated bicarbonate solution, 100 mL of TDW, 2×100 mL KHSO$_4$ 1M, and 100 mL TDW, dried over Na$_2$SO$_4$ and evaporated to dryness yielding 10.36 g (92% yield) of yellow oil. $^1$H NMR (CDCl$_3$, 300 MHz) δ 2.38 (t, 2H), 2.51 (t, 2H), 3.10 (s, 3H), 3.56 (s, 3H), 7.15-7.50 (m, 15H).

(c)) Trityl-Thiopropanal

LiAlH$_4$ (2.014 g, 0.053 mol) was added in portions to a solution of 10.36 g (0.0265 mol) of Trityl-thiopropanoic acid hydroxamate in 260 mL dry diethyl ether under cooling in ice bath and argon atmosphere. The reaction mixture was stirred for 2 hours (monitored by TLC PE:EA=1:1). 560 mL of EA were added followed by addition of 560 mL of KHSO$_4$ 1M. The mixture was stirred for additional 30 minutes. The organic layer was collected and washed with 390 mL of KHSO$_4$ 1M and 390 mL of saturated NaCl, dried over Na$_2$SO$_4$ and evaporated yielding 7.68 g (87% yield) of white solid. $^1$H NMR (CDCl$_3$, 300 MHz, 298K) δ 2.36 (t, 2H), 2.46 (t, 2H), 7.15-7.50 (m, 15H), 9.55 (t, 1H).

Trityl Thiobutyral (a)) Trityl-Thiobutyric Acid:

Trityl mercaptan (36.13 g, 0.131 mol) was added stepwise to a suspension of NaH (11.5 g, 60% in mineral oil 0.288 mol) in 100 mL DMF under cooling and nitrogen atmosphere, the reaction mixture was stirred 30 minutes after the addition was completed. Then, a solution of bromobutric acid (21.88 g, 0.131 mol) dissolved in 150 mL DMF was added stepwise. After the addition was completed the reaction mixture was stirred for 30 minutes and then cooling and nitrogen atmosphere were stopped and the reaction mixture was sealed and left overnight. Then, 500 mL chloroform were added and the mixture was washed with 4×200 mL of saturated solution of KHSO$_4$ and 4×300 mL of water (the solid that precipitate during the washings should also be collected with the organic layer). The organic layer was evaporated and the oily product (that contained DMF traces) was triturated by adding 300 mL TDW and stirring vigorously for few minutes. The product was collected by filtration, washed by TDW and dried by suction. The crude product was purified as follows: 200 mL of PE was added to the white solid and the mixture was stirred for 15 minutes. The solid was collected by filtration and dried in vacuo yielding 36.82 g (77.6% yield) of white powder. $^1$H NMR (CDCl$_3$, 300 MHz, 298K) δ 1.67 (m, 2H), 2.22 (t, 2H), 2.30 (t, 2H), 7.10-7.50 (m, 15H).

b) Trityl-Thiobutyric Acid Hydroxamate

A solution of N,O dimethylhydroxylamine hydrochloride (0.83 g, 0.0084 mol) in 20 mL DMF was added to a mixture of 2.77 g (0.0076 mol) of Trityl-thiobutric acid and PyBoP (4.39 g, 0.0084 mol). DIEA (4 mL, 0.023 mol) was added and the clear solution was stirred for 3 hours (pH should be monitored and kept basic). EA (50 mL) was added to the stirred solution followed by 90 mL of saturated bicarbonate solution. The organic layer was collected and washed with additional two portions of 40 mL of saturated bicarbonate solution, 40 mL of water, 2×40 mL KHSO$_4$ 1M, and 40 mL water, dried over Na$_2$SO$_4$ and evaporated to dryness yielding 3.06 g (quantitative yield) of yellow oil. $^1$H NMR (CDCl$_3$, 300 MHz) δ 1.74 (m, 2H), 2.23 (t, 2H), 2.38 (t, 2H), 3.13 (s, 3H), 3.63 (s, 3H), 7.10-7.50 (m, 15H).

c) Trityl-Thiobutanal

LiAlH$_4$ (0.574 g, 0.0151 mol) was added in portions to a solution of 3.06 g (0.0075 mol) of the hydroxamate in 100 mL dry diethyl ether under cooling in ice bath and argon atmosphere. The reaction mixture was stirred for 1 hour (monitored by TLC PE:EA=1:1). 150 mL of EA were added followed by addition of 150 mL of KHSO$_4$ 1M. The mixture was stirred for additional 30 minutes. The organic layer was collected and washed with 100 mL of KHSO$_4$ 1M and 100 mL of saturated NaCl, dried over Na$_2$SO$_4$ and evaporated yielding 1.90 g (73% yield) of white solid. $^1$H NMR (CDCl$_3$, 300 MHz, 298K) δ 1.66 (m, 2H), 2.22 (t, 2H), 2.38 (t, 2H) 7.15-7.50 (m, 15H), 9.61 (t, 1H).

Trityl Thiovaleric Aldehyde (a)) Trityl-Thiovaleric Acid:

Trityl mercaptan (36.13 g, 0.131 mmol) was added stepwise to a suspension of NaH (11.5 g, 60% in mineral oil 0.288 mol) in 100 mL DMF under cooling and nitrogen atmosphere, the reaction mixture was stirred 30 minutes after the addition was completed. Then, a solution of bromovaleric acid (23.71 g, 0.131 mol) dissolved in 150 mL DMF was added stepwise. After the addition was completed the reaction mixture was stirred for 30 minutes and then cooling and nitrogen atmosphere were stopped and the reaction mixture was sealed and left overnight. Then, 500 mL chloroform were added and the mixture was washed with 4×200 mL of saturated solution of KHSO$_4$ and 4×300 mL of water (the solid that precipitate during the washings should also be collected with the organic layer). The organic layer was evaporated resulting in a solid product (that contained DMF traces). 300 mL TDW were added and the mixture was stirred vigorously for few minutes. The product was collected by filtration and partially dried by suction. The crude product was purified as follows: 200 mL of PE was added to the white solid and the mixture was stirred for a few minutes. The solid was collected by filtration and dried in vacuo yielding 45.06 g (91% yield) of white powder. $^1$H NMR (CDCl$_3$, 300 MHz, 298K) δ 1.41 (m, 2H), 1.58 (m, 2H), 2.18 (m, 4H), 7.15-7.45 (m, 15H). MS (ES) m/z 376.

(b)) Trityl-Thiovaleric Acid Hydroxamate

A solution of N,O dimethylhydroxylamine hydrochloride (0.7 g, 0.0071 mol) in 16 mL DMF was added to a mixture of 2.45 g (0.0065 mol) of Trityl-thiovaleric acid and PyBoP (3.73 g, 0.0071 mol). DIEA (3.4 mL, 0.02 mol) was added and the clear solution was stirred for 3 hours (pH should be monitored and kept basic). EA (50 mL) was added to the stirred solution followed by 90 mL of saturated bicarbonate solution. The organic layer was collected and washed with additional two portions of 40 mL of saturated bicarbonate solution, 40 mL of water, 2×40 mL KHSO$_4$ 1M, and 40 mL water, dried over Na$_2$SO$_4$ and evaporated to dryness yielding 3.06 g (quantitative yield) of yellow oil. $^1$H NMR (CDCl$_3$, 300 MHz) δ 1.74 (m, 2H), 2.23 (t, 2H), 2.38 (t, 2H), 3.13 (s, 3H), 3.63 (s, 3H), 7.10-7.50 (m, 15H).

(c)) Trityl Thiovaleric Aldehyde

LiAlH$_4$ (0.574 g, 0.0151 mol) was added in portions to a solution of 3.06 g (0.0075 mol) of the hydroxamate in 100 mL dry diethyl ether under cooling in ice bath and argon atmosphere. The reaction mixture was stirred for 1 hour (monitored by TLC PE:EA=1:1). 150 mL of EA were added followed by addition of 150 mL of KHSO$_4$ 1M. The mixture was stirred for additional 30 minutes. The organic layer was collected and washed with 100 mL of KHSO$_4$ 1M and 100 mL of saturated NaCl, dried over Na$_2$SO$_4$ and evaporated yielding 1.90 g (73% yield) of white solid. $^1$H NMR (CDCl$_3$, 300 MHz, 298K) δ 1.66 (m, 2H), 2.22 (t, 2H), 2.38 (t, 2H) 7.15-7.50 (m, 15M), 9.61 (t, 1H).

Trityl Thiohexanal:

(a)) Trityl-Thiohexanoic Acid:

Trityl mercaptan (36.13 g, 0.131 mol) was added stepwise to a suspension of NaH (11.5 g, 60% in mineral oil 0.288 mol) in 100 mL DMF under cooling and nitrogen atmosphere, the reaction mixture was stirred 30 minutes after the addition was completed. Then, a solution of bromohexanoic acid (25 g, 0.128 mol) dissolved in 150 mL DMF was added stepwise. After the addition was completed the reaction mixture was stirred for 30 minutes and then cooling and nitrogen atmosphere were stopped and the reaction mixture was sealed and left overnight. Then, 500 mL chloroform were added and the mixture was washed with 4×200 mL of saturated solution of $KHSO_4$ and 4×300 mL of water (the solid that precipitate during the washings should also be collected with the organic layer). The organic layer was evaporated and the product (that contained DMF traces) was triturated by adding 300 mL TDW and stirring vigorously for few minutes. The product was collected by filtration, washed by TDW and dried by suction. The crude product was purified as follows: The solid was dissolved in a mixture of 150 ml of $CHCl_3$ and 200 ml of PE, and the solution was evaporated. The oil obtained was triturated by addition of 100 ml PE and 50 ml of $Et_2O$ then 50 ml $Et_2O$ and 50 ml PE. The solid was collected by filtration and dried in vacuo yielding 33.92 g (68% yield) of white powder. $^1H$ NMR ($CDCl_3$, 300 MHz, 298K), δ 1.31 (m, 2H), 1.37 (m, 2H), 1.50 (m, 2H), 2.15 (t, 2H), 2.26 (t, 2H), 7.15-7.50 (m, 15H).

(b)) Trityl-Thiohexanoic Acid Hydroxamate

A solution of N,O dimethylhydroxylamine hydrochloride (1.23 g, 0.0126 mmol) in 25 mL DMF was added to a mixture of 4.47 g (0.0115 mol) of Trityl-thiohexanoic acid and PyBoP (6.56 g, 0.0126 mol). DIEA (6 mL, 0.0344 mol) was added and the clear solution was stirred for 3 hours (pH should be monitored and kept basic). EA (70 mL) was added to the stirred solution followed by 130 μL of saturated bicarbonate solution. The organic layer was collected and washed with additional two portions of 60 mL of saturated bicarbonate solution, 60 mL of water, 2×60 mL $KHSO_4$ 1M, and 60 mL water, dried over $Na_2SO_4$ and evaporated to dryness yielding 4.29 g (86% yield) of yellow oil. $^1H$ NMR ($CDCl_3$, 300 MHz) δ 1.29 (m, 2H), 1.44 (m, 2H), 1.51 (m, 2H), 2.16 (t, 21), 2.33 (t, 2H), 3.15 (s, 3H), 3.65 (s, 3H) 7.15-7.50 (m, 15H).

(c)) Trityl-Thiohexanal $LiAlH_4$ (0.75 g, 0.0198 mol) was added in portions to a solution of 4.29 g (0.0099 mol) of the hydroxamate in 130 mL dry diethyl ether under cooling in ice bath and argon atmosphere. The reaction mixture was stirred for 1 hour (monitored by TLC PE:EA=1:1). 200 mL of EA were added followed by addition of 200 mL of $KHSO_4$ 1M. The mixture was stirred for additional 30 minutes. The organic layer was collected and washed with 140 mL of $KHSO_4$ 1M and 140 mL of saturated NaCl, dried over $Na_2SO_4$ and evaporated yielding 3.45 g (93% yield) of white solid. $^1H$ NMR ($CDCl_3$, 300 MHz, 298K) δ 1.38 (m, 2H), 1.49 (m, 2H), 1.60 (m, 2H), 2.15 (t, 2H), 2.34 (t, 2H), 7.10-7.55 (m, 15H), 9.71 (t, 1H).

Trityl thioacetaldehyde and trityl thiopentanal were prepared by procedures similar to those described above.

TABLE 1 structure and MS characterization of a library according to the present invention, the preparation of which is showed in Scheme 5 above.

| compound number | $R^6$ | $R^7$ | $R^8$ | m | n | M.W calc. | M.W Obsvd. |
|---|---|---|---|---|---|---|---|
| 1 | L-hydroxy benzyl | L-Benzyl | Z# | 4 | 5 | 649.87 | 653.3 |
| 2 | L-hydroxy benzyl | L-Benzyl | Z | 5 | 4 | 649.87 | 653.3 |
| 3 | L-Benzyl | D-hydroxy benzyl | Z | 4 | 5 | 649.87 | 653.2 |
| 4 | L-Benzyl | D-hydroxy benzyl | Z | 5 | 4 | 649.87 | 653.3 |
| 5 | D-hydroxy benzyl | L-Benzyl | Z | 4 | 5 | 649.87 | 653.2 |
| 6 | D-hydroxy benzyl | L-Benzyl | Z | 5 | 4 | 649.87 | 653.2 |
| 7 | D-Benzyl | L-hydroxy benzyl | Z | 4 | 5 | 649.87 | 653.3 |
| 8 | D-Benzyl | L-hydroxy benzyl | Z | 5 | 4 | 649.87 | 653.2 |
| 9 | L-hydroxy benzyl | D-Benzyl | Z | 4 | 5 | 649.87 | 653.2* |
| 10 | L-hydroxy benzyl | D-Benzyl | Z | 5 | 4 | 649.87 | 653.3 |
| 11 | L-hydroxy benzyl | L-hydroxy benzyl | Z | 6 | 6 | 707.94 | 711.79 |
| 12 | D-hydroxy benzyl | D-hydroxy benzyl | Z | 6 | 6 | 707.94 | 711.85 |
| 13 | L-hydroxy benzyl | D-hydroxy benzyl | Z | 6 | 6 | 707.94 | 711.91 |
| 14 | D-hydroxy benzyl | L-hydroxy benzyl | Z | 6 | 6 | 707.94 | 711.43 |
| 15 | L-hydroxy benzyl | L-Benzyl | Z | 6 | 6 | 691.94 | 694.8 |
| 16 | D-hydroxy benzyl | D-Benzyl | Z | 6 | 6 | 691.94 | 693.41 |
| 17 | L-hydroxy benzyl | D-Benzyl | Z | 6 | 6 | 691.94 | 693.79 |
| 18 | D-hydroxy benzyl | L-Benzyl | Z | 6 | 6 | 691.94 | 693.91 |
| 19 | L-Benzyl | L-hydroxy benzyl | Z | 6 | 6 | 691.94 | 693.79 |
| 20 | D-Benzyl | D-hydroxy benzyl | Z | 6 | 6 | 691.94 | 693.6 |
| 21 | L-Benzyl | D-hydroxy benzyl | Z | 6 | 6 | 691.94 | 693.23** |
| 22 | D-Benzyl | L-hydroxy benzyl | Z | 6 | 6 | 691.94 | 693.23** |
| 23 | L-Benzyl | L-Benzyl | Z | 6 | 6 | 675.95 | 677.24** |
| 24 | D-Benzyl | D-Benzyl | Z | 6 | 6 | 675.95 | 677.23** |
| 25 | L-Benzyl | D-Benzyl | Z | 6 | 6 | 675.95 | N.D |
| 26 | D-Benzyl | L-Benzyl | Z | 6 | 6 | 675.95 | 677.30** |

Z = benzyloxy carbonyl
*The peak was obtained relatively with low intensity.
**The peak was analyzed with HRMS.

Mass spectrometric analysis: The discrepancy between the calculated and the observed mass as described in Table 1 ranges between 1.5 to 2.5 amu. These results may indicate the existence of reduced non cyclic molecule rather then the oxidized desired macrocycles. In order to negate this possibility the peaks were analyzed by splitting (marked with ** in Table 1). This analysis yielded the expected MW values with a discrepancy of only 0.3 amu. Furthermore, these molecules were also analyzed by MS-MS and a fragment indicating a disulfide bridge was found:

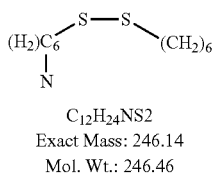

$C_{12}H_{24}NS_2$
Exact Mass: 246.14
Mol. Wt.: 246.46

Example 2

Biological Activity of Heterocyclic Compounds having IGF-I Receptor

Many cancers are known to be associated with abnormal (over) activity of the IGF-1R receptor. Therefore inhibiting the phosphorylation of this kinase is a promising approach for selectively inhibiting cancer cell proliferation.

Three amino acids in the activation loop of IGF-1 receptor were identified, by structural analysis, to be important for substrate binding. These amino acids are Tyr in position 1135, Tyr 1163 and Tyr 1131-corresponding to positions 1162, 1163 and 1158, respectively in IRK. It was hypothesized that mimicking these amino acids would result in an interruption of the kinase-substrate interaction and thus inhibit IGF-1R-dependent phosphorylation. A small library of compounds based on the compound of formula:

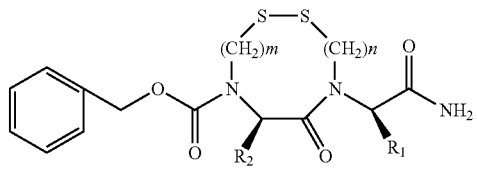

was synthesized with amino acid residue mimicking Tyr and Phe positioned on rings of varying sizes, in different orders and having different chiralities (Tyr, D-Tyr Phe or D-Phe). The ring structures were substituted with carbobenzoxy at position $R_3$ (mimicking Tyr at position 1135 in IGF1-R) and Tyrosine side chain at position $R_1$, mimicking Tyr at position 1136. The library of compounds is depicted in Table 2:

TABLE 2

| Compound name | $R_2$ | $R_1$ | n | m | Inhibition of IGF-1R phosphorylation | Inhibition of MCF7 proliferation (% of control) |
|---|---|---|---|---|---|---|
| SIB1 | Phe | Tyr | 4 | 5 | − | 62 |
| SIB2 | Phe | Tyr | 5 | 4 | − | 100 |
| SI3 | DTyr | Phe | 4 | 5 | | |
| SIB4 | DTyr | Phe | 5 | 4 | − | 100 |
| SIB5 | Phe | DTyr | 4 | 5 | + | 50 |
| SIB6 | Phe | DTyr | 5 | 4 | + | 100 |
| SIB7 | Tyr | DPhe | 4 | 5 | + | 31 |
| SIB8 | Tyr | DPhe | 5 | 4 | −/+ | 100 |
| SIB9 | DPhe | Tyr | 4 | 5 | + | 55 |
| SIB10 | DPhe | Tyr | 5 | 4 | + | 90 |

The compounds were screened for their activity in inhibition of the proliferation of breast cancer cell line MCF7. Crude mixtures comprising compounds SIB3, SIB7 and SIB10 were found to be active in inhibition of proliferation, with SIB7 having the formula given bellow being the most active.

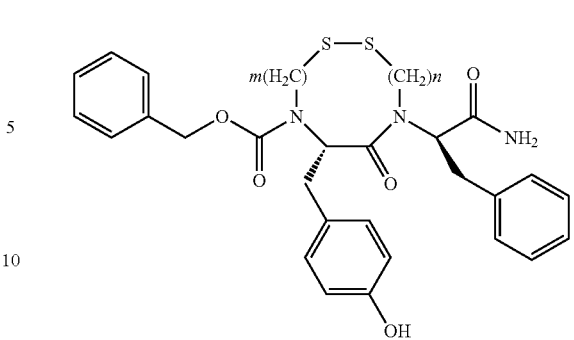

A compound termed "SIB7" was found to be active in inhibiting the proliferation of several cancer cell lines and was found to inhibit IGF-1 dependent phosphorylation of both the IGF-1 receptor itself (which serves as its own substrate in trans-phosphorylation) and the downstream element ERK.

A stick model of the active compound SIB7, superimposed on the amino acids of the IGF-1 activation loop (FIG. 1) shows that the compound SIB7 can faithfully mimic at least the two amino acids Tyr at position 1135 and Tyr at position 1136.

Figure 2:
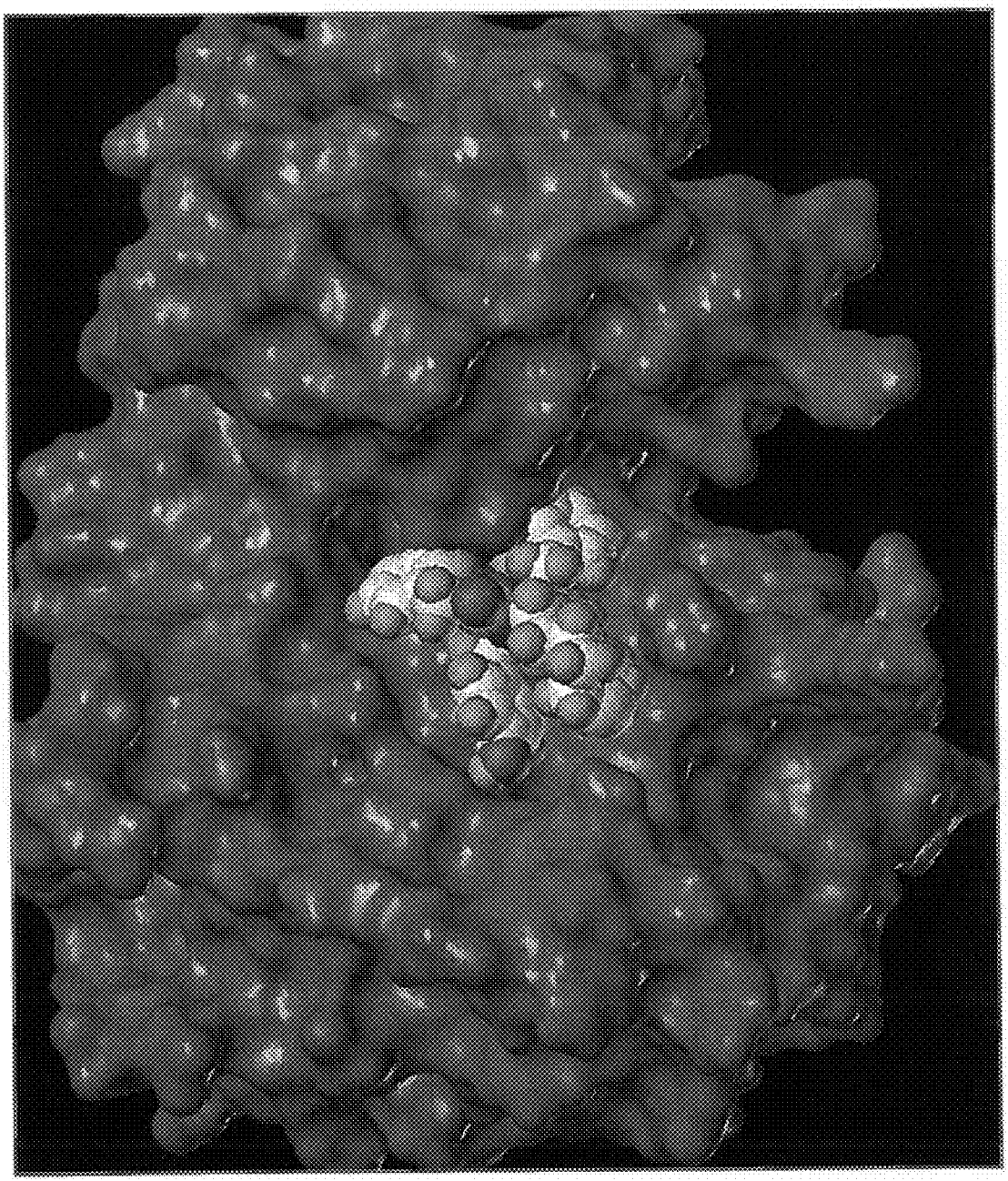
FIG. 2: shows a FlexX space filed model of SIB7 docking into the substrate binding site of IGF-IR.

A FlexX run on the TRIPOSE™ software (FIG. 2) indicated that compound SIB7 can dock into the binding site of IGF-1R, thus showing that it is capable of preventing the trans-phosphorylation of one IGF-1R molecule by another.

Example 3

Inhibition of IGF-1 Receptor and ERK Phosphorylation by the Compound of the Invention SIB7

Western Blot Analysis

MCF-7 cells were starved in a serum-free medium for 14 h and exposed to varying concentrations of SIB7 (2.5-100 uM dissolved in DMSO) for the last 5 h of starvation. Cells were stimulated with IGF-1 (Song/ml) for 10 minutes and lysed with lysis buffer containing 20 mM Tris HCl (pH 7.5), 10% Glycerol, 1 mM EDTA, 1 mM EGTA, 1% TritonX100, 0.5 mM $Na_3VO_4$, 10 mM β-glycerophosphate, 5 mM NaPPi, 50 mM NaF, 1 mM benzamidine and protease inhibitor cocktail (Sigma). Equal amounts of protein (25 μg) were separated by 8% SDS-polyacrylamide gel electrophoresis, and the resolved proteins were electrotransferred to nitrocellulose membrane. Membranes were incubated with 3% BSA in TBST (25 mM Tris-HCl (pH 7.4), 0.17M NaCl, and 0.2% Tween 20) for 1 h at room temperature followed by incubation with primary antibodies (see below) at 4° C. overnight. Membranes were then washed with TBST and probed with HRP-conjugated secondary antibodies at room temperature for 1 h. Membranes were washed several times with TBST and visualized using enhanced chemiluminescence kit (Supper signal, Pierce).

The respective phosphorylation of IGF-1R and ERK was determined by Western blotting using anti-phosphoIGF-IR (Tyr 1131)/Insulin receptor (Tyr1146) antibody (Cell signaling) and anti-diphospho (Thr183/Tyr185)ERK1&2 (Sigma). Blots were stripped and reprobed with anti-IGF1R/IR and anti-ERK (Santa Cruz biotechnology), respectively. Quantification of the blots was preformed using the Image J analysis system. Histograms represent the ratio between the levels of the phosphorylated protein (pIGF-IR and pERK) and the levels of the total proteins (IGF-1R and ERK), respectively.

Figure 3A:
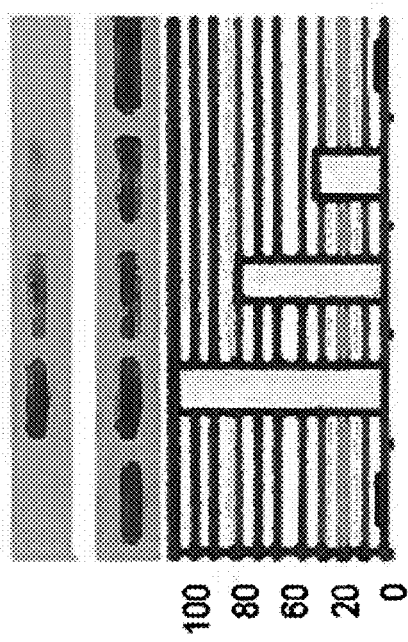
FIG. 3A: shows the phosphorylation levels of IGF-1R in the presence and absence of SIB7.
Figure 3B:
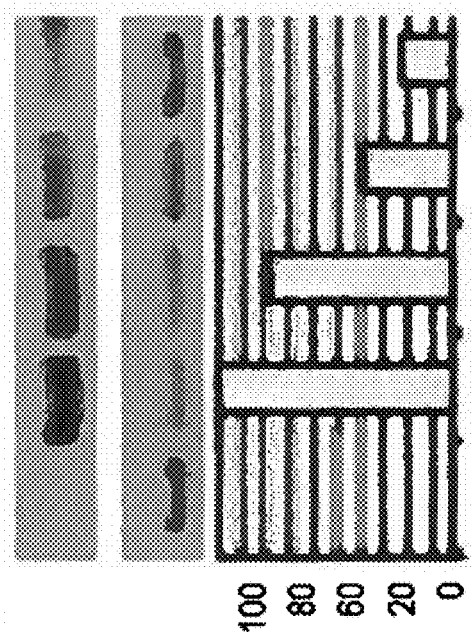
FIG. 3B: shows the phosphorylation levels of ERK, a downstream element of 1GF1R, in the presence and absence of SIB7.

The results are shown in FIG. 3A and FIG. 3B. As can be seen the ratio of both the phosphorylated IGF-1 receptor to non-phosphorylated receptor (FIG. 3A) as well as the ratio of phosphorylated ERK to non-phosphorylated ERK (FIG. 3B), decreased, in a dose-dependent manner, with increasing concentration of the compound SIB7. This result indicates that SIB7 was capable of interfering with the trans-phosphorylation of the IGF-1 receptor itself and of interfering with the phosphorylation of its down-stream elements-ERK, probably due to interruption of the kinase-substrate interaction, due to docking of the compound in lieu of the native substrate (which may be either the ERK or another IGF-IR molecule) in the substrate binging site of IGF-1R., thus inhibiting the phosphorylation or trans-phosphorylation.

Example 4

Inhibition of Proliferation of Tumor Cells by SIB7

The following Human solid tumors cell lines, which proliferation is known to be dependent on the phosphorylation activity of IGF1R, were used: MDA231 (estrogen receptor deficient human breast cancer), MCF-7 (estrogen receptor positive human breast cancer), PC3 and DU145 (hormone refractory prostate cancer cells), colon cancer cell line HT29 and PANC1 (pancreas cancer cells) were obtained from the American Type Culture Collection. These cell lines were grown in RPMI 1640 medium supplemented with penicillin (100 U/ml), streptomycin (100 μg/ml), glutamine (2 mM) and 10% endotoxin free fetal calf serum (Hyclone).

A suspension of the cells at $2 \times 10^4$ cells/ml was prepared in the above-described culture mediums and distributed 0.180 ml per well (about 4000 cells/well) in the wells of 96 well, flat bottom, tissue culture microtiter plates.

A series of compound stock solutions were prepared by diluting a 10 mM solution of the compound in 100% DMSO with phosphate buffered saline (PBS) containing 0.1% bovine serum albumin (BSA) to a concentration of 400 μM. The concentration of compound in each stock solution was adjusted to ten times the desired concentration of the compound in the assay mixture. 0.020 ml of each compound stock solution was added to the corresponding wells about 3 hours after cell addition, with three replicates for each concentration. In addition, PBS containing 0.1% BSA solution with either no added compound (NT) or final 0.1% DMSO was used as a control. The plates were labeled and incubated for 72-80 hours at 37° C. in a 5% $CO_2$ humidified incubator.

The medium discarded and the wells were fixed with 4% formaldehyde in PBS (formalin was obtained from Fisher Scientific; Catalog No. HC200-1) (0.2 ml/well) for at least 30 minutes. The wells were washed one time with borate buffer (0.2 ml/well) (0.1M, pH 8.5). Freshly filtered 1% methylene blue solution (0.06 ml/well) was then added to the wells and incubated for 10 minutes at room temperature. The wells were then washed five times with tap water, after which the wells were dried completely. 0.20 ml/well of 0.1 N HCl was added to extract the color. After overnight extraction, the O.D. was read at 595 nm to determine the number of cells per well. The procedure for counting cells is described in greater detail in Oliver et al, (1989), the teachings of which are incorporated herein by reference.

The proliferation results are shown in the attached Table 3 and in FIG. 4 for proliferation of MCF-7 cell line.

As can be seen, SIB37, which was shown to inhibit. IGF-1R-associated phosphorylation (see above example) was capable of inhibiting the proliferation of a number of cancer cell lines, which proliferation is known to be dependent on IGF-IR activity.

TABLE 3

Inhibition of cancer cell line proliferation by compound SIB7:

| Cell line | $IC_{50}$ (μM) |
|---|---|
| DU145 | 85 |
| PC3 | 48 |
| HT29 | — |
| MCF7 | 16 |
| MDA231 | 37 |
| PANC1 | 42 |

It will be appreciated by a person skilled in the art that the present invention is not limited by what has been particularly shown and described hereinabove. Rather, the scope of the invention is defined by the claims which follow:

REFERENCES

Adang A. E. P. and Hermkens P. H. H., *Curr. Med. Chem.* 8:985 (2001);
Beeley N. R. A., *Drug Disc. Today* 5:354 (2000);
Bunin B. A. and Ellman J. A., *J. Am. Chem. Soc.* 114:11997 (1992);
Campian E. et al, *Bioorg. Med. Chem Lett.* 8:2357 (1998);
Furka A. et al. *Int. J Pept. Protein. Res.* 37:487-493 (1991);
Geysen H. M. et al. *Proc. Natl. USA,* 11: 3998 (1984);
Houghten R. A., *Proc. Natl. USA,* 82:5131 (1985);
Kumar S. et al. *Prot. Sci.* 2:10-19 (2000);
Lipinsky C. A. et al., *Adv. Drug Deliv. Rev.* 23, 3 (1997);
Lipinsky C. A., *Chimia* 52:503 (1998);
Morrison K. L. and Weiss G. A., *Curr. Opin. Chem. Biol.* 5:302-307 (2001);
Oliver et al. *J. Cell Sci.,* 92: 513 (1989);
Rink H., *Tetrahedron Lett.* 2a: 3787 (1987);
Winter et al. *Nature* 2: 756 (1982);

What is claimed is:

1. A combinatorial library comprising a plurality of compounds represented by the structure of formula I:

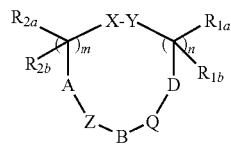

wherein
A and D are each $CH_2$,
B is C=O;
X and Y together form a group represented by the formula:

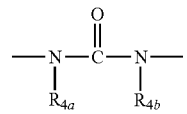

$R_{1a}$, $R_{1b}$, $R_{2a}$, $R_{2b}$, $R_{4a}$ and $R_{4b}$ are independently of each other hydrogen or a linear or branched chain alkyl; m and n are independently of each other an integer of 1-6;
Q is Z is

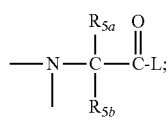

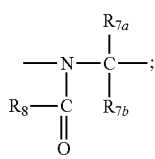

$R_{5a}$, $R_{5b}$, $R_{7a}$, $R_{7b}$, $R_8$ and $R_{9a}$ are independently of each other hydrogen, a linear or branched chain alkyl, cycloalkyl, aryl, aralkyl, heterocyclyl, heteroaryl, acyl, carboxyalkyl, carboxyaryl, benzyl, hydroxybenzyl, benzyloxycarbonyl, a side chain of a natural or unnatural amino acid or a peptide; and L is hydrogen, $OR_{10}$, or $NHR_{11}$ wherein $R_{10}$ and $R_{11}$ are independently of each other hydrogen, a linear or branched chain alkyl, a side chain of a natural or unnatural amino acid, a peptide or a solid support;

such that the compound is represented by the structure

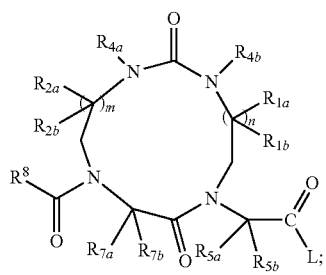

or a pharmaceutically acceptable salt, hydrate or solvate thereof.

2. The library according to claim 1, wherein each member of the library differs from the other by the nature or chirality of the substituents on the ring.

3. The library according to claim 1, wherein each member of the library comprises at least one pharmacophore associated with a biological activity, wherein said biological activity is proliferation, differentiation, phenotype alteration, uptake, secretion, metabolism, gene expression, protein expression, or any combination thereof.

4. The library according to claim 1, comprising at least one compound of formula I wherein $R_8$ is benzyloxycarbonyl.

5. The library according to claim 1, comprising at least one compound of formula I wherein L is $NH_2$ or OH.

6. The library according to claim 1, comprising at least one compound of formula I wherein $R_{1a}$, $R_{1b}$, $R_{2a}$ and $R_{2b}$ are each hydrogen.

7. The library according to claim 1, comprising at least one compound of formula I wherein at least one of $R_{1a}$, $R_{1b}$, $R_{2a}$ and $R_{2b}$ is a substituted alkyl.

8. The library according to claim 7, wherein the alkyl of claim 7 is substituted by an aryl or by an amino.

9. The library according to claim 1, comprising at least one compound of formula I wherein $R_{5a}$ and $R_{5b}$ are each hydrogen.

10. The library according to claim 1, comprising at least one compound of formula I wherein $R_8$ is a side chain of a natural or unnatural amino acid.

11. The library according to claim 1, comprising at least one compound of formula I wherein $R_8$ is an alkyl which is substituted by an amino, an unsubstituted or substituted aryl, or a combination thereof.

12. The library according to claim 1, comprising at least one compound of formula I wherein Q is

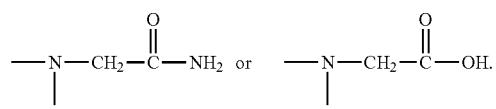

13. The library according to claim 1, comprising at least one compound of formula I wherein
Z is

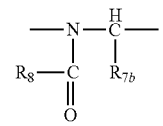

wherein $R_{7b}$ is the residue of a natural or unnatural amino acid, and $R_8$ is $—OCH_2Ph$ or

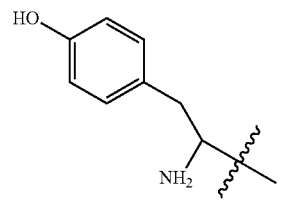

14. A method of identifying a compound having a beneficial biological activity, said method comprising the steps of: designing a combinatorial library according to claim 1, wherein each member of the library comprises at least one pharmacophore associated with a biological activity, wherein said biological activity is proliferation, differentiation, phenotype alteration, uptake, secretion, metabolism, gene expression, protein expression, or any combination thereof; synthesizing a plurality of compounds from said combinatorial library; and screening said compounds for candidates having said biological activity.

15. The method according to claim 14, wherein each member of the library differs from the other by the nature or chirality of the substituents on the ring.

16. The method according to claim 14, wherein said biological activity is achieved by modulation of a cellular component.

17. The method of claim 16, wherein said pharmacophore is complementary to a domain in said cellular component which is associated with said biological activity.

18. The method according to claim 14, wherein said designing step further comprises: identifying a domain in a cellular component which is associated with said biological activity; and virtually screening said combinatorial library for lead compounds having a pharmacophore complementary to said domain.

19. The method according to claim 18, wherein said virtual screening step comprises virtual screening with a computer readable data storage material encoded with computer readable data comprising three-dimensional structural determinants defining said domain.

20. The method according to claim 18, wherein said computer readable data storage material is further encoded with a computer program logic for controlling a processor, said computer program logic comprising a procedure that enables said processor to identify a member of said combinatorial library having a pharmacophore complementary to said domain.

21. The method according to claim 16, wherein said cellular component is a protein, a nucleic acid or a combination thereof.

* * * * *

UNITED STATES PATENT AND TRADEMARK OFFICE
CERTIFICATE OF CORRECTION

| | | |
|---|---|---|
| PATENT NO. | : 8,198,218 B2 | Page 1 of 1 |
| APPLICATION NO. | : 12/474318 | |
| DATED | : June 12, 2012 | |
| INVENTOR(S) | : Gilon | |

It is certified that error appears in the above-identified patent and that said Letters Patent is hereby corrected as shown below:

Title Page:
Item (56) References Cited, OTHER PUBLICATIONS, Qvit et al. reference, after "Library" change "Dsicovery" to -- Discovery --.

Column 41:
Line 6 (claim 20), after "claim" change "18" to -- 19 --.

Signed and Sealed this
Thirty-first Day of July, 2012

David J. Kappos
*Director of the United States Patent and Trademark Office*